(12) United States Patent
Zhou et al.

(10) Patent No.: US 11,622,964 B2
(45) Date of Patent: Apr. 11, 2023

(54) METHOD FOR DESTROYING CELLULAR MECHANICAL HOMEOSTASIS AND PROMOTING REGENERATION AND REPAIR OF TISSUES AND ORGANS, AND USE THEREOF

(71) Applicant: INSTITUTE OF ZOOLOGY, CHINESE ACADEMY OF SCIENCES, Beijing (CN)

(72) Inventors: Qi Zhou, Beijing (CN); Wei Li, Beijing (CN); Zhengquan He, Beijing (CN); Liu Wang, Beijing (CN)

(73) Assignee: INSTITUTE OF ZOOLOGY, CHINESE ACADEMY OF SCIENCES, Beijing (CN)

( * ) Notice: Subject to any disclaimer, the term of this patent is extended or adjusted under 35 U.S.C. 154(b) by 17 days.

(21) Appl. No.: 16/965,401

(22) PCT Filed: Jan. 29, 2019

(86) PCT No.: PCT/CN2019/073622
§ 371 (c)(1),
(2) Date: Jul. 28, 2020

(87) PCT Pub. No.: WO2019/144967
PCT Pub. Date: Aug. 1, 2019

(65) Prior Publication Data
US 2021/0069177 A1  Mar. 11, 2021

(30) Foreign Application Priority Data

Jan. 29, 2018 (CN) .......................... 201810082885.2
Jan. 29, 2018 (CN) .......................... 201810083566.3

(51) Int. Cl.
| | | |
|---|---|---|
| A61K 31/4745 | (2006.01) | |
| A61P 1/16 | (2006.01) | |
| A61P 17/02 | (2006.01) | |
| A61P 11/00 | (2006.01) | |

(52) U.S. Cl.
CPC ............ *A61K 31/4745* (2013.01); *A61P 1/16* (2018.01); *A61P 11/00* (2018.01); *A61P 17/02* (2018.01)

(58) Field of Classification Search
CPC ........ A61K 31/4745; A61P 1/16; A61P 17/02; A61P 11/00
See application file for complete search history.

(56) References Cited

U.S. PATENT DOCUMENTS

| | | | | |
|---|---|---|---|---|
| 8,697,385 B1 * | 4/2014 | Stefanovic | ............... | C12Q 1/37 435/23 |
| 2017/0065577 A1 * | 3/2017 | Sander | ............... | A61K 31/4745 |
| 2017/0296585 A1 | 10/2017 | Castro et al. | | |

FOREIGN PATENT DOCUMENTS

| | | |
|---|---|---|
| CN | 101056974 | 10/2007 |
| CN | 106190980 | 12/2016 |
| CN | 110090300 | 8/2019 |
| EP | 2 777 703 | 9/2014 |
| WO | 2010/120785 | 10/2010 |

OTHER PUBLICATIONS

Liu et al., Blebbistatin inhibits contraction and accelerates migration in mouse hepatic stellate cells, 159 British J. of Pharmacology, 304-315 (2010) (Year: 2010).*
Notice of Reasons for Refusal dated Sep. 14, 2021, in corresponding Japanese Patent Application No. 2020-562820, with English translation.
Extended European Search Report dated Oct. 20, 2021, in corresponding European Patent Application No. 19743774.2.
Atluri, K. etaL, "Blebbistatin-Loaded Poly($_{D,L}$-lactide-*co*-glycolide) Particles For Treating Arthrofibrosis", ACS Biomaterials Science and Engineering, vol. 2, 2016, pp. 1097-1107.
International Search Report dated Apr. 29, 2019 in International (PCT) Application No. PCT/CN2019/073622.
Southern, B.D., "Matrix-Driven Myosin II Mediates the Pro-Fibrotic Fibroblast Phenotype", Journal of Biological Chemistry, vol. 291, 2016, pp. 1-27.
Cai, Le et al. "Nonmuscle Myosin-Dependent Synthesis of Type I Collagen", Journal of Molecular Biology, vol. 401, No. 4, 2010, pp. 564-578.
Kamiya, Akihide et al., "Stem and progenitor cell systems in liver development and regeneration", Hepatology Research, vol. 45, 2015, pp. 29-37.

(Continued)

*Primary Examiner* — Timothy R Rozof
(74) *Attorney, Agent, or Firm* — Wenderoth, Lind & Ponack, L.L.P.

(57) ABSTRACT

Disclosed are a method for destroying cellular mechanical homeostasis and the use thereof, especially disclosed is a method for destroying cellular mechanical homeostasis by using a Myosin inhibitor thereby leading to cell softening and reduction of fibrosis in tissues and organs. Also disclosed are a method for promoting regeneration and repair of tissues and organs and the use thereof. The Myosin inhibitor can destroy the homeostasis of the cellular mechanical stress system, reduce the rigidity of tissues and organs in a pathological state, and stimulate stress and regeneration reactions similar to those in the regeneration processes in lower organisms; and can use the characteristics to greatly inhibit fibrosis during the organ damage and to promote the regeneration and repair of tissues and organs, and meanwhile can use stress response to greatly improve the ability of cellular genetic repair. The Myosin inhibitor is preferably (−)-Blebbistatin, or a derivative thereof (−)-Blebbistatin O-Benzoate. The method requires only a single small molecule or single factor treatment, and is simple in operation and good in repeatability, and can be used as a new method to stimulate stress response, to stimulate regeneration response, to improve the ability of cellular genetic repair and/or promote regeneration and repair of tissues and organs.

2 Claims, 23 Drawing Sheets

(56) References Cited

OTHER PUBLICATIONS

Liu, Zhenan et al., "Blebbistatin inhibits contraction and accelerates migration in mouse hepatic stellate cells", British Journal of Pharmacology 2010, vol. 159, pp. 304-315.

* cited by examiner

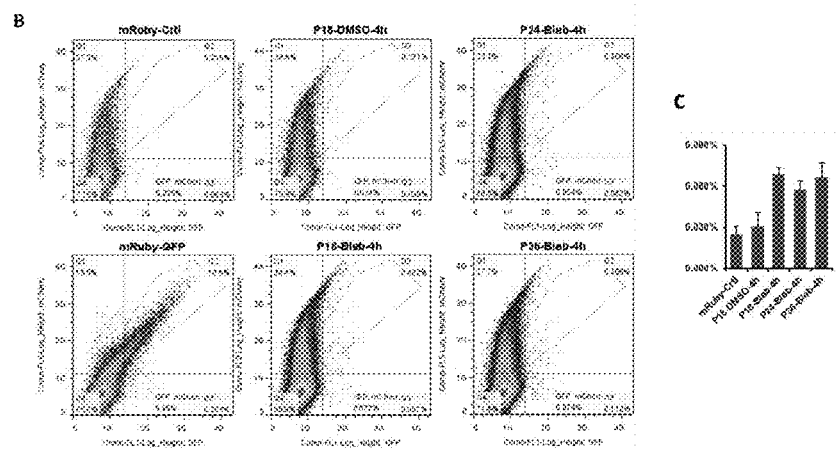
Figs. 11(B) and (C)
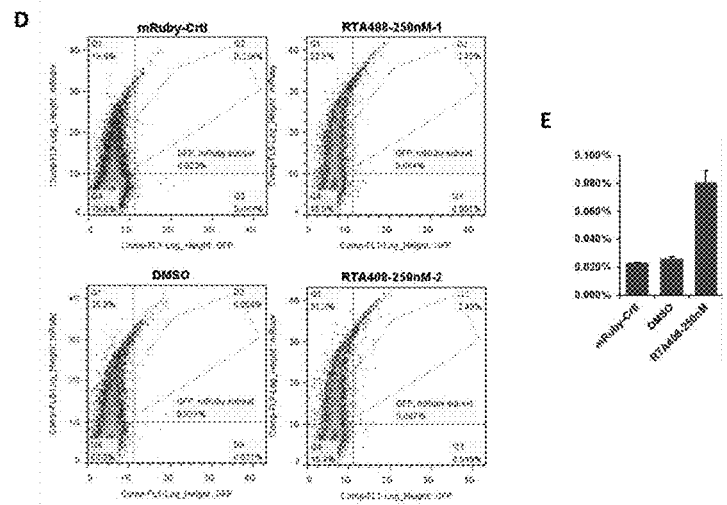
Figs. 11(D) and (E)

METHOD FOR DESTROYING CELLULAR MECHANICAL HOMEOSTASIS AND PROMOTING REGENERATION AND REPAIR OF TISSUES AND ORGANS, AND USE THEREOF

TECHNICAL FIELD

The invention relates to the field of biotechnology, in particular to a method for destroying the cellular mechanical homeostasis and the related applications, and also relates to a method for promoting regeneration and repair of tissues and organs and the related applications.

BACKGROUND TECHNIQUE

As for multicellular organisms, the organs and tissues are composed of parenchymal cells and mesenchymal cells and the extracellular matrix secreted thereby. The parenchymal cells refer to the main structural and functional cells of tissues and organs (e.g., the parenchymal cells of the brain are neurons, and the parenchymal cells of the liver are hepatocytes); and the mesenchymal cells and extracellular matrix constitute the mesenchymal part of tissues and organs (mainly including mesenchymal cells, collagen, laminin, fibronectin, elastin, proteoglycans, glycoproteins, glycosaminoglycans), mainly playing a role in mechanical support and ligation; extracellular matrix constitutes and maintains the microenvironment of cellular physiological activities, and is a bridge of signal transduction between cells, participating in and regulating a variety of physiological and pathological processes, and playing an important role in the process of tissue repair, regeneration and fibrosis.

In the regeneration process of the lower organisms, an damage leads to a rapid stress response, the expression levels of a series of stress proteins such as heat shock protein family are upregulated, and the stress response occurs within 24 hours of damage; then regeneration response is triggered at 2-2.5 days after injury, and some regeneration-initiating related genes and tissue-specific genes are upregulated; in the final stage of regeneration, the specific differentiated tissue cells appear, thereby regenerating new tissues.

For evolutionary reasons, mammals have very limited regeneration ability. Damage of tissue cells in higher mammals causes degeneration, necrosis and inflammatory response in the tissue cells. If the damage is small, normal parenchymal cells surrounding the damaged tissue cells will undergo proliferation and repair, thereby completely restoring normal tissue structure and function. However, if a large damage or repeated damage exceeds the regeneration and repair ability of the surrounding parenchymal cells, in order to prevent excessive bleeding and reduce the risk of infection, the body initiates a severe stress protection mechanism to produce blood clotting response, immune response and inflammatory response; and the fibrous connective tissue (extracellular matrix) in the mesenchymal part is promoted to proliferate vastly so as to repair the defective tissue, thereby accompanying with pathological changes of fibrosis. Although the proliferating fibrous connective tissue repairs the defective tissue and protects the relative integrity of the tissue to the greatest extent, this repair not only inhibits normal regeneration and repair so that the repair has no structure and function of the original organ, but also may cause the fibrosis and hardening of an organ so as to lose the function due to this excessive, too strong and uncontrolled repair response.

All over the world, fibrosis of tissues and organs is the main cause of disability and death from many diseases, and plays an important role in the occurrence and development of related diseases of major organs in human body. According to relevant statistics, nearly 45% of the patients who die from various diseases in the United States can be attributed to fibroplasia of tissues and organs. Therefore, controlling the fibrosis process in mammals is an important idea for treating various diseases.

Stress fiber is a microfilament bundle structure widely existed in eukaryotic cells, and consists of a large number of microfilaments arranged in parallel; and stress fiber is closely related to the adhesion between cells or between cells and the surface of the substrate, and it plays an important role in cell morphogenesis, cell differentiation and tissue formation, and the like. The components of stress fiber are actin, myosin, tropomyosin and $\alpha$-actinin. The main mechanical stress system of cells is composed of stress fibers, extracellular matrix, cell membrane receptors (such as integrins), linker complexes of nuclear skeleton and cytoskeleton, nuclear lamina, and chromosome skeleton, etc. The mechanical stress system imparts regulation of mechanical hardness of cells, participates in the induction, transmission and production of mechanical forces inside and outside a cell, and regulates the assembly, distribution and expression of genetic material. The homeostasis of mechanical stress system is one of the characteristic indexes of specific cells. The homeostasis of cellular mechanical stress system helps to maintain and establish specific cell properties, maintain and stabilize specific genetic regulation and expression characteristics of cells; breaking the cellular mechanical homeostasis, as a kind of cell damage, stimulates the stress response of cells, and stimulates strong ability of cellular damage repair.

The invention utilizes a no loss and no bleeding manner to destroy the homeostasis of cellular mechanical stress system, thereby destroying the mechanical hardness of the cells, softening the cells, and improving the remodelability of the cell fate; and it is similar to that stem cells may be converted into cells with different destinies under certain conditions.

The invention also utilizes a no loss and no bleeding manner to destroy the homeostasis of cellular mechanical stress system, thereby stimulating stress response and regeneration response similar to those in the regeneration process of lower organisms; and the ability of cytogenetic repair may be greatly improved by utilizing the stress response. Since the treatment of the invention is simple, it can be used as a new method for mobilizing somatic cells to participate in cell renewal, inhibiting tissue fibrosis, and improving the ability of tissue repair and organ regeneration during the lesion damage of mammals. It can also be used as a new means to improve the ability of homologous recombination and the ability of double-strand breaking mediated homologous recombination in cells of the body.

CONTENTS OF THE INVENTION

The present invention has been accomplished on the basis of the inventors' following findings: a myosin inhibitor may destroy the homeostasis of cellular mechanical stress system, destroy the mechanical hardness of cells, cause cell softening, and reduce fibrosis of tissues and organs, thereby completing the present invention.

Accordingly, in one embodiment, the invention relates to use of a myosin inhibitor in destroying the homeostasis of cellular mechanical stress system.

In one embodiment, the invention also relates to use of a myosin inhibitor in destroying cellular mechanical hardness.

In one embodiment, the invention also relates to use of a myosin inhibitor in softening cells.

In one embodiment, the invention also relates to use of a myosin inhibitor in reducing fibrosis in tissues and organs.

In one embodiment, the invention also relates to use of a myosin inhibitor in the preparation of a medicament or reagent for destroying the homeostasis of cellular mechanical stress system.

In one embodiment, the invention also relates to use of a myosin inhibitor in the preparation of a medicament or reagent for destroying cellular mechanical hardness.

In one embodiment, the invention also relates to use of a myosin inhibitor in the preparation of a medicament or reagent for softening cells.

In one embodiment, the invention also relates to use of a myosin inhibitor in the preparation of a medicament or reagent for reducing fibrosis in tissues or organs.

In one embodiment, the invention further relates to use of a myosin inhibitor in the preparation of a medicament or reagent for treating a disease associated with disorder of the homeostasis of cellular mechanical stress system, disorder of the cellular mechanical hardness, or fibrosis in tissues or organs.

In one embodiment, the myosin inhibitor is (−)-blebbistatin, abbreviated as Ble, or Bleb, or Blebb.

In one embodiment, the myosin inhibitor is (−)-blebbistatin o-benzoate, abbreviated as S-Bleb-OB.

The (−)-blebbistatin (also denoted as (S)-(−)-blebbistatin, or S-Bleb) used in the present invention is a cell permeable inhibitor acting on non-myosin II ATPase, the inhibitor does not inhibit myosin light chain kinase, but inhibits the constriction of cleavage furrows, and does not interfere with the assembly of mitosis or contractile rings. The structural formula of S-Bleb is as shown in formula (I) with the molecular weight of 292.33.

The (−)-blebbistatin o-benzoate (also denoted as (S)-(−)-blebbistatin o-benzoate, or S-Bleb-OB) used in the present invention is a derivative of (−)-blebbistatin, and its structural formula is as the formula (II).

Formula (I)

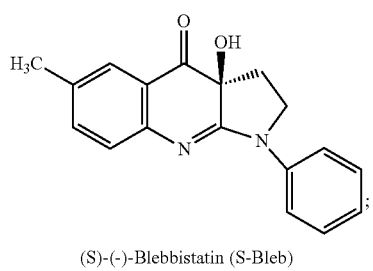

(S)-(−)-Blebbistatin (S-Bleb)

Formula (II)

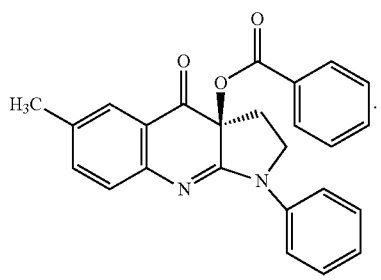

(S)-(−)-Blebbistatin O-Benzoate
(S-Bleb-OB)

In one embodiment, the fibrosis is a fibrosis in any tissue or organ.

In one embodiment, the fibrosis is a hepatic fibrosis, pulmonary fibrosis, muscle fibrosis, skin scars or nerve tissue scars.

In one embodiment, the hepatic fibrosis is a hepatic fibrosis caused by alcoholic hepatitis, viral hepatitis, non-alcoholic steatohepatitis, toxin or drug, autoimmune liver disease, hepatic congestion, inherited metabolic disease, or other causes.

In one embodiment, the pulmonary fibrosis is a pulmonary fibrosis caused by various causes, including pulmonary fibrosis caused by inhalation of inorganic dust, radiation damage, inhalation of organic dust, drug damage or other causes; and idiopathic pulmonary fibrosis.

In one embodiment, the muscle fibrosis is a muscle fibrosis caused by a genetic factor or a congenital factor.

In one embodiment, the skin scar is a skin lesion caused by a physical, biological, chemical factor or the like; or a skin fibrosis caused by a genetic factor.

In one embodiment, the nerve tissue scar is a nerve tissue fibrosis caused by gliosis and other factors resulting from damage of the central nervous system by mechanical damage, hypoxia, hypoglycemia, infection, poisoning, and the like.

In one embodiment, the central nervous system comprises brain tissue or spinal cord.

The method of the invention requires only a single small molecule or single factor treatment, and is simple in operation and good in repeatability, and can be used as a new method for promoting the inhibition of fibrosis in tissues or organs in a mammal during pathological change and damage.

The present invention has been accomplished on the basis of the inventors' following findings: a myosin inhibitor may destroy the homeostasis of cellular mechanical stress system, and stimulate stress response and regeneration response similar to those in the regeneration process of lower organisms; and the stress response can be utilized to greatly improve the ability of cytogenetic repair, thereby completing the present invention.

Accordingly, in one embodiment, the invention relates to use of a myosin inhibitor in stimulating stress response.

In one embodiment, the invention relates to use of a myosin inhibitor in stimulating stress response by destroying the homeostasis of cellular mechanical stress system.

In one embodiment, the invention also relates to use of a myosin inhibitor in stimulating regeneration response.

In one embodiment, the invention relates to use of a myosin inhibitor in stimulating regeneration response by destroying the homeostasis of cellular mechanical stress system.

In one embodiment, the invention also relates to use of a myosin inhibitor in improving the ability of cytogenetic repair.

In one embodiment, the invention relates to use of a myosin inhibitor in improving the ability of cytogenetic repair by destroying the homeostasis of cellular mechanical stress system.

In one embodiment, the stimulation of stress response causes to activate high genetic damage repair response, thereby improving the up-regulation of the homologous recombination repair gene in the body and improving the recombination ability.

In one embodiment, the invention also relates to use of a myosin inhibitor in promoting regeneration and repair of tissues and organs.

In one embodiment, the invention relates to use of a myosin inhibitor in promoting regeneration and repair of tissues and organs by destroying the homeostasis of cellular mechanical stress system.

In one embodiment, the invention also relates to use of a myosin inhibitor in the preparation of a medicament or reagent for stimulating stress response, stimulating regeneration response, improving the ability of cytogenetic repair, and/or promoting regeneration and repair of tissues and organs.

In one embodiment, the invention also relates to use of a myosin inhibitor in the preparation of a medicament or reagent for stimulating stress response, stimulating regeneration response, improving the ability of cytogenetic repair, and/or promoting regeneration and repair of tissues and organs by destroying the homeostasis of cellular mechanical stress system.

In one embodiment, the invention further relates to use of a myosin inhibitor in the preparation of a medicament or reagent for treating a disease associated with stress response, regeneration response, the ability of cytogenetic repair, and/or regeneration and repair of tissues and organs.

In one embodiment, the disease is scleroderma.

In one embodiment, the myosin inhibitor is (−)-blebbistatin, abbreviated as Ble, or Bleb, or Blebb.

In one embodiment, the organ is a liver.

The method of the invention requires only a single small molecule or single factor treatment, and is simple in operation and good in repeatability, and can be used as a new method for stimulating stress response, stimulating regeneration response, improving ability of cytogenetic repair, and/or promoting regeneration and repair of tissues and organs.

In one embodiment, the invention relates to a method for destroying the homeostasis of cellular mechanical stress system, destroying cellular mechanical hardness, softening cells, or reducing fibrosis in tissues or organs, the method comprises: administering a myosin inhibitor to a subject in need thereof.

In one embodiment, the invention relates to a medicament for treating a disease associated with disorder of the homeostasis of cellular mechanical stress system, disorder of the cellular mechanical hardness, or fibrosis in tissues or organs, which comprises a myosin inhibitor.

In one embodiment, the invention relates to a method for stimulating stress response, stimulating regeneration response, and/or improving the ability of cytogenetic repair, the method comprises: administering a myosin inhibitor to a subject in need thereof.

In one embodiment, the invention relates to a method for promoting regeneration and repair of tissues and organs, the method comprises: administering a myosin inhibitor to a subject in need thereof.

In one embodiment, the invention relates to a method for treating a disease associated with stress response, regeneration response, and/or the ability of cytogenetic repair, the method comprises: administering a myosin inhibitor to a subject in need thereof.

In one embodiment, the invention relates to a medicament for stimulating stress response, stimulating regeneration response, and/or improving the ability of cytogenetic repair, wherein the medicament comprises: a myosin inhibitor.

In one embodiment, the invention relates to a medicament for promoting regeneration and repair of tissues and organs, wherein the medicament comprises: a myosin inhibitor.

In one embodiment, the invention relates to a medicament for treating a disease associated with stress response, regeneration response, and/or the ability of cytogenetic repair, wherein the medicament comprises: a myosin inhibitor.

BRIEF DESCRIPTION OF THE DRAWINGS

FIG. 2A shows the dosing regimen in the treatment of chronic mild hepatic fibrosis models. FIG. 2B shows the immunohistochemistry of Sirius red staining of liver tissues and the corresponding quantitative analysis for oil treatment group (left) and $CCl_4$-induced mild liver damage model group (right) (n=3 mice for oil treatment group, n=5 female mice for $CCl_4$ modeling group). FIG. 2C shows the immunohistochemical analysis of H&E (top panel) and Sirius red (bottom panel) (n=6 mice per group) for the therapeutic effects. FIG. 2D is a polarized light analysis of Sirius red staining results. Data are expressed as mean±SD. *$P<0.05$, $P<0.01$, *$P<0.001$ (student t-test).

FIG. 3A shows the dosing regimen in the treatment of chronic severe hepatic fibrosis models. FIG. 3B shows Sirius red staining analysis of $CCl_4$ modeling effect (n=5 mice for the oil treatment group, and n=4 mice for the $CCl_4$ modeling group). FIGS. 3C-3D respectively show therapeutic effect analysis with Sirius red histochemistry staining and type I collagen immunofluorescence staining (FIG. 3C, n=at least 5 mice per group; FIG. 3D, n=3 mice per group). FIGS. 3E-3F show analysis of the changes of fibrosis-related indicators during treatment from the transcriptional level (n=3 mice per group, the significant analysis from RNAseq data). Data are expressed as mean±SD. *$P<0.05$, $P<0.01$, *$P<0.001$ (student t-test).

FIG. 4A shows the blood biochemical analysis of liver damage and liver function related indicators in the treatment group and control group (n=3 mice per group). FIG. 4B shows the expression of ALB protein in the treated and control groups by using Alb Cre mouse labelled hepatocytes. FIG. 4C shows the analysis of hepatocyte proliferation in the treatment group and the control group by co-staining ALB and Ki-67. FIG. 4D shows the analysis of apoptosis of liver tissue in the treatment group and the control group by TUNEL staining.

FIG. 5A, the mechanical rigidity of fresh liver tissue before and after treatment is measured by Mark 10 ESM303 Tensile Compression Force Tester (WT group, n=4 mice; other mouse groups, n=at least 6 mice). FIG. 5B shows the content and topological distribution of fibers in the treatment group and the control group by second harmonic intravital scanning (n=5 mice per group). Data are expressed as mean±SD. *P<0.05, P<0.01, *P<0.001 (student t-test).

FIG. 6A is a flow diagram of Bleb treatment of hepatic injury induced by bile duct ligation. FIG. 6B shows the state of the mice in the treatment group and the control group. FIG. 6C shows the circumstances about Sirius red histochemistry staining, and αSMA immunofluorescence analysis of collagenous fiber accumulation and activation of myofibroblasts at day 15 of the treatment (Sirius red, n=6 mice per group; αSMA, n=at least 4 mice per group). FIG. 6D shows that Sirius red histochemistry staining displaying collagenous fiber accumulation at day 30 of the treatment (n=at least 3 mice per group). FIG. 6E shows the proliferation of liver tissue cells in the treatment group and the control group. Data are expressed as mean±SD. *P<0.05, P<0.01, *P<0.001 (student t-test).

FIG. 7A shows a flow diagram of Bleb treatment of scleroderma induced by bleomycin. FIG. 7B shows changes in skin structure at day 7 of the treatment. FIG. 7C shows melanin accumulation and new hair growth after treatment. FIG. 7D shows H&E histochemistry and Masson staining analysis of skin structure and fiber accumulation in the hardened zone. FIG. 7E shows analysis of the thickness of epidermal and dermal in the hardened zone after treatment (n=at least 3 mice per group). FIG. 7F shows analysis of the number of hair follicles in the hardened zone after treatment (n=at least 3 mice per group). FIG. 7G shows analysis of the proliferation in the hardened zone after treatment. FIG. 7H shows the identification of hair follicle and gland regeneration. FIG. 7I shows the identification of hair follicle proliferation. FIGS. 7J-K show the immunofluorescence analysis of FGF9 and NeuN expression.

FIG. 8A shows a flow diagram of Bleb treatment of pulmonary fibrosis induced by bleomycin. FIG. 8B shows that Bleb treatment significantly increases survival rate of mice with pulmonary fibrosis. FIGS. 8C-8D are small animal CT images showing that Bleb treatment significantly inhibits non-volume reduction. The top panels of FIG. 8E show that Bleb treatment relieves lung damage by hematoxylin-eosin staining (HE). The bottom panels of FIG. 8E show that Bleb treatment relieves pulmonary fibrosis by Sirius Red staining.

FIG. 10 (A) shows transcriptome analysis at the time point of 6 hours after treatment of human fibroblasts with 5-50 µM (−)-blebbistatin, wherein the DNA replication-related and homologous recombination-related genes, mismatching repair-related genes, and nucleotide excision repair and the base excision repair genes are significantly upregulated. FIG. 10 (B) shows further analysis reveals that almost all of the important genes involved in homologous recombination are significantly upregulated.

FIGS. 11(A)-(E) show the application of the high genetic damage repair response activated by the stimulation of stress response by (−)-blebbistatin in the process of improving the homologous recombination repair of genes in the body. The figures show the process of improving the homologous recombination repair of genes in the body caused by high genetic damage repair response accompanying with the stimulation of stress response.

FIGS. 13(A)-(F) show that a myosin inhibitor inhibits transformation of mouse hepatic stellate cells (mHSCs) to myofibroblasts induced by TGF-β1 and extracellular matrix synthesis; wherein FIG. 13(A) shows the specific schemes of Examples 9-1; in FIG. 13(B), the non TGF-β1 induction group is used as a negative control and labeled as "Con", and the TGF-β1 induction groups are respectively treated with DMSO and Bleb, and labeled as "TGFB+DMSO", "TGFB+Bleb", wherein FIG. 1 is the result of immunofluorescence staining, and FIG. 1I is the result of quantitative PCR. With three replicates, FIG. 13 (C) shows that Bleb significantly inhibits transformation of mouse MEFs to myofibroblasts induced by TGF-β1 and extracellular matrix synthesis; FIG. 13 (D) shows that Bleb significantly inhibits transformation of mouse primary mesenchymal cells of different organs to myofibroblasts induced by TGF-β1 and extracellular matrix synthesis; in FIG. 13 (E), the non TGF-β1 induction group is used as a negative control and labeled as "Con", and the TGF-β1 induction groups are respectively treated with DMSO and Bleb, and labeled as "TGFB+DMSO", "TGFB+Bleb", with three replicates. FIG. 13(F) and FIG. 13(G) show that different compounds including Bleb and S-Bleb-OBd etc. have an inhibitory effect on the activation of myofibroblasts induced by TGF-β1.

SPECIFIC EMBODIMENTS

Figure 1:
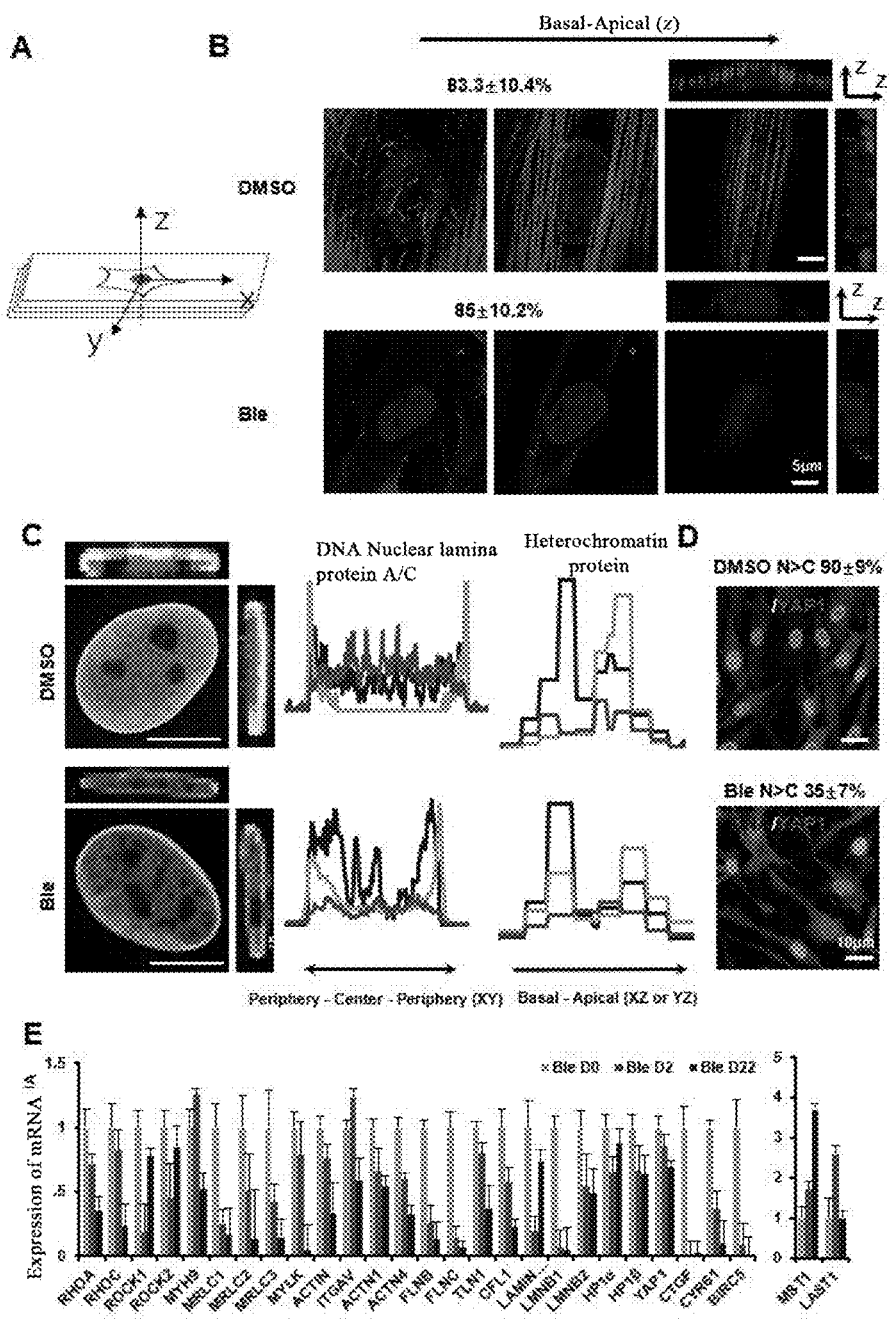
FIG. 1 shows the graphs about the destruction of homeostasis of the cellular machinery system and the induction of cell softening by a myosin inhibitor.
Figure 1:
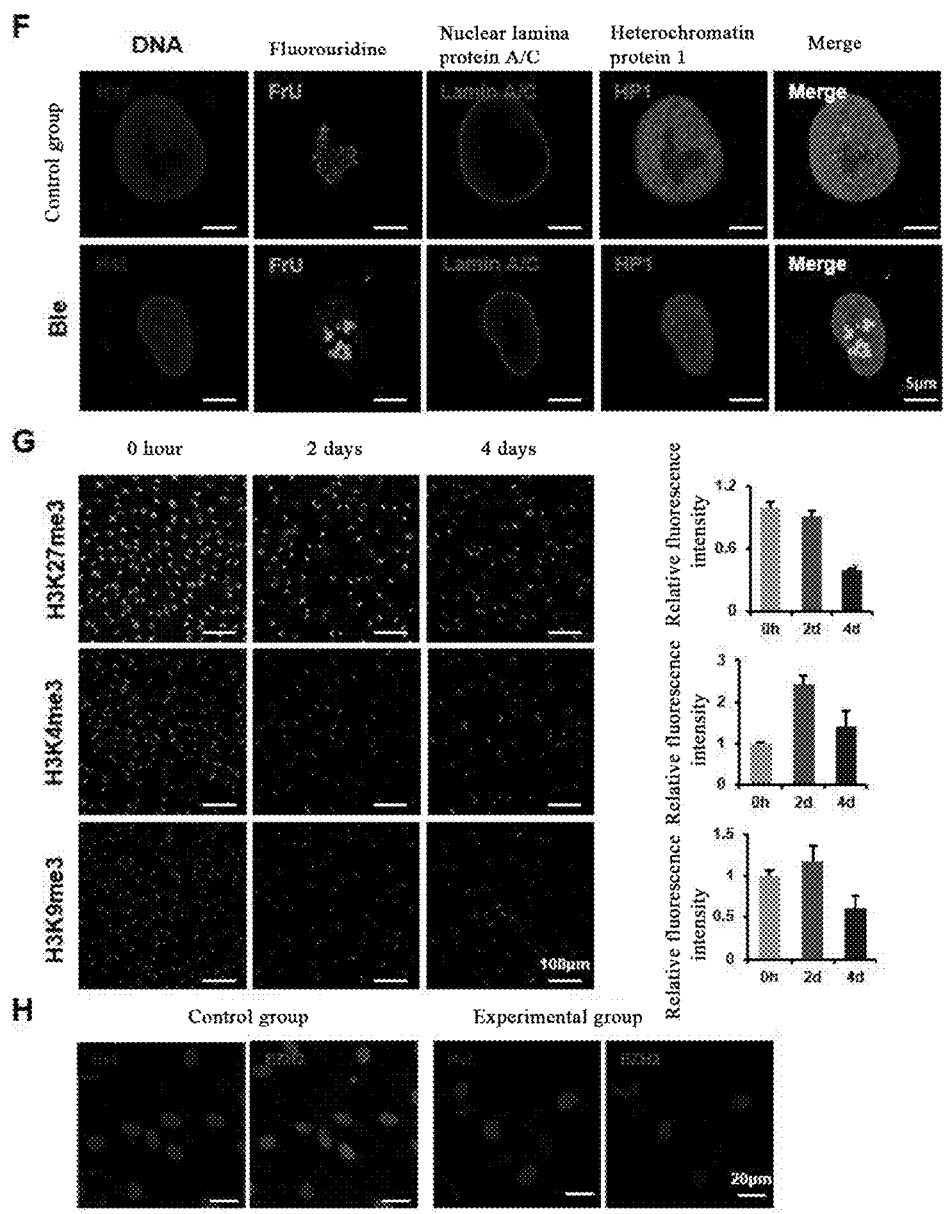

Specific examples of the present invention will be described in more detail below with reference to the accompanying drawings. Although the drawings show specific examples of the invention, it should be understood that the present invention may be implemented in various forms and should not be limited by the examples set forth herein. On the contrary, these examples are provided so that this invention may be more fully understood, and the scope of the invention can be fully conveyed to those skilled in the art.

It should be noted that certain words are used in the description and claims to refer to particular components. Those skilled in the art will appreciate that a skilled person may refer to the same component by different nouns. The present specification and claims do not use the difference in nouns as a way to distinguish components, but rather use the functional difference between components as a criterion to distinguish them. The word "comprise/comprising" or "include/including" as used throughout the specification and claims is an open-ended term, and should be interpreted as "include/including but not limited to". The following description of the present specification is intended to illustrate the preferred embodiments of the invention. The description is for the purpose of the general principles of the specification and is not intended to limit the scope of the invention. The scope of the invention is defined by the appended claims.

As used herein, "substantially free" with respect to a particular component is to mean that the particular component has not been purposefully formulated into the composition, and/or is present only as a contaminant or in trace amounts. Accordingly, the total amount of the particular component resulting from any accidental contamination of the composition is less than 0.05%, preferably less than 0.01%. A composition in which the amount of the particular component is not detectable by standard analytical method is the most preferable.

As used herein, "a" or "an" may mean one or more. As used in the claims, when used in conjunction with the word "comprising", the word "a" or "an" may mean one or more than one.

The word "or" is used in the claims to mean "and/or" unless it is specifically indicated that it refers to an alternative or the alternatives are mutually exclusive, although the disclosure of the application supports the definition of referring to only alternative and "and/or". As used herein, "another" may mean at least a second or more.

Throughout this application, the term "about" is used to indicate that the value includes an inherent change in the error range of a device, and the method is used to determine the value or change existing between subjects.

In this application, "differentiation" is a process by which less specialized cells become more specialized cell types. "Dedifferentiation" is a cellular process in which a partially or terminally differentiated cell returns to an earlier stage of development, such as a multipotency or pluripotency. "Transdifferentiation" is the process of converting one differentiated cell type into another differentiated cell type. Typically, transdifferentiation occurs by programming while the cell does not undergo an intermediate pluripotent stage, i.e., the cell is programmed directly from one differentiated cell type to another differentiated cell type.

As used herein, the term "subject" or "subject in need" refers to a mammal, preferably a human, of a male or female of any age that needs cell or tissue transplantation. Typically, a subject needs cell or tissue transplantation (also referred to herein as a receptor), due to a disorder, or pathology, or undesired condition, state or syndrome, or abnormal of the body, morphology, or physiology is suitable for treatment via cell or tissue transplantation.

Some of the terms used herein are defined as follows:

BMP4: bone morphogenetic protein 4 (bmp4).

High-glucose DMEM: a high-glucose DMEM medium (dulbecco's modified eagle medium), i.e., a commercial medium containing various glucoses and amino acids, it is developed on the basis of MEM medium.

N2B27: a cell culture medium with definite components, it is a mixture of DMEM/F12 basal medium and neurobasal basal medium in a ratio of 1:1, and contains N2 additive and B27 additive. It is reported that N2B27 facilitates the differentiation of mouse embryonic stem cells into the nerve direction.

DMEM/F12: a commercial basal medium obtained by mixing DMEM medium and F12 medium in a ratio of 1:1, it is suitable for culture of clonal density.

Neurobasal: a commercial basal medium that facilitates the culture of nerve cells.

GlutaMAX: a cell culture additive that may directly replace L-glutamine in a cell culture medium.

Double antibody: penicillin and streptomycin are two commonly used antibiotics in cell culture to prevent bacterial contamination during cell culture.

N2 Additive: a commercial serum-free cell culture additive.

B27 Additive: a commercial serum-free cell culture additive.

KOSR: a commercial KnockOut serum replacement (KOSR).

CHIR99021: a GSK-3α/β inhibitor commonly used as an activator of Wnt signaling pathway.

A83-01: a selective TGF-β inhibitor that significantly inhibits the activity of ALK4, ALK5 and ALK7.

$CCl_4$: carbon tetrachloride, an organic compound used as a reagent for inducing liver damage.

Bleomycin: a chemotherapeutic drug used as a reagent to induce skin scleroderma and pulmonary fibrosis models.

Sirius Red: the combination of a strong acid dye with collagen molecules enhances the birefringence phenomenon, thereby allowing collagenous fibers with different colors and forms to be distinguished.

Masson staining: a method for identifying collagenous fibers, including mixing two or three anionic dyes, wherein after staining the collagenous fibers are blue, and the muscle fibers are red. It is one of the staining methods for displaying the fibers and the inflammatory factors in tissues.

α-SMA: α-smooth muscle actin, also known as Acta2, is a marker protein of myofibroblasts (the main cell that synthesizes and secretes extracellular matrix such as collagenous fibers) in fibrotic tissues, and is used to identify the activation of myofibroblasts. It is also expressed in vascular smooth muscle cells under normal physiological condition.

DMSO: dimethyl sulfoxide, an organic solvent.

PEG400: polyethylene glycol 400, as a liquid it has broad compatibility with various solvents, and is also a good solvent and solubilizer widely used in liquid preparations such as oral solutions, eye drops, and the like.

Tween 80: sorbitan monooleate polyoxyethylene ether, it is used as a solubilizer or emulsifier for injections and oral solutions.

The present invention relates to use of a myosin inhibitor in destroying the homeostasis of cellular mechanical stress system, destroying cellular mechanical hardness, softening cells, or reducing fibrosis in tissues or organs.

In a specific embodiment of the invention, organ fibrosis is, for example, hepatic fibrosis. Hepatic fibrosis is an abnormal proliferation of connective tissue in the liver caused by various physiological and pathogenic factors in the pathophysiological process, accompanying with a large amount of extracellular matrix accumulation in liver tissue. Any type of liver damage is accompanied with varying degrees of hepatic fibrosis during liver repair and healing. If the damage factor cannot be removed for a long time, it will affect liver regeneration and repair, and normal liver function, but also develop into liver cirrhosis and even liver cancer due to a long term process of firbrosis. Anti-fibrosis treatment mainly includes: removal of pathogenic factors for primary disease, such as anti-hepatitis virus treatment, anti-parasitic (such as schistosomiasis) treatment, alcohol withdrawal and good living habits. The fibrosis itself may be treated by inhibiting inflammation, lipid peroxidation, or inhibiting the proliferation and activation of hepatic stellate cells, and promoting collagen degradation. etc. However, there is currently no safe and effective means for treating and preventing hepatic fibrosis in clinical practice. Therefore, it is urgent to find and develop new anti-fibrotic targets and their regulation means. In this application, there is no specific limitation on the cause of hepatic fibrosis, such as hepatic fibrosis caused by alcoholic hepatitis, viral hepatitis, nonalcoholic steatohepatitis, toxins or drugs, autoimmune liver diseases, hepatic congestion, inherited metabolic diseases, or other pathogenesis. In this application, myosin is inhibited to destroy the cytoskeletal homeostasis, thereby softening cells, and small molecule inhibitors of mysoin, such as (−)-blebbistatin (abbreviated as Ble, Bleb or Blebb), or (−)-blebbistatin O-Benzoate are verified to have the effect of anti-fibrosis and promotion of regeneration and repair in a variety of liver damage models.

The present invention shows that myosin inhibitors may significantly inhibit hepatic fibrosis during mild liver damage. The present invention shows that myosin inhibitors may significantly inhibit hepatic fibrosis during chronic severe liver damage. The present invention shows that myosin inhibitors may significantly promote cell proliferation after liver damage and reduce apoptosis during liver damage. The present invention shows that myosin inhibitors promote liver regeneration and maintain liver function by inhibiting fibrosis of liver damage, promoting hepatocyte proliferation, and reducing apoptosis. Further, the present invention shows that a stress response induced by an inhibitor of myosin inhibits tissue fibrosis, promotes hepatocyte proliferation, and promotes liver regeneration. The present invention shows that an inhibitor of myosin may be used to reduce tissue rigidity during liver damage.

Further, the present invention shows that the inhibitors of myosin may significantly inhibit the accumulation of collagenous fibers caused by bile duct ligation, and promote the proliferation of hepatocytes during bile duct ligation.

In a specific embodiment of the invention, organ fibrosis refers to pulmonary fibrosis, which is a pathological change characterized by fibroblast proliferation, a large amount of extracellular matrix accumulation accompanied with inflammatory damage and destruction of tissue structure; i.e., a structural abnormality (scar formation) caused by abnormal repair of the damaged normal alveolar tissue. Pulmonary fibrosis will seriously affect the respiratory function of human body, the clinical manifestations are various types of dyspnea, and the respiratory function of the patient will get worse with the aggravation of the disease and lung damage. It is reported that the morbidity and mortality of idiopathic pulmonary fibrosis has increased worldwide year by year, and the average survival time after diagnosis is less than 3 years, and is higher than most tumors, so it is also called a "tumor-like disease". Therefore, it has important application value in the treatment and prevention of pulmonary fibrosis-related diseases to find new targets and drugs that may effectively inhibit pulmonary fibrosis. In the present invention, there is no further limitation on the cause of pulmonary fibrosis, and a pulmonary fibrosis mentioned herein refers to the pulmonary fibrosis caused by various causes, including the pulmonary fibrosis caused by inhalation of inorganic dust, radiation damage, inhalation of organic dust, drug damage, or other causes; and idiopathic pulmonary fibrosis.

In the present invention, myosin inhibitor may be used to inhibit tissue damage and fibrosis during lung damage.

The present invention relates to use of a myosin inhibitor in the preparation of a medicament or reagent for treating a disease associated with stress response, regeneration response and/or the ability of cytogenetic repair. In a specific embodiment, the disease associated with the regeneration and repair of tissues and organs is scleroderma. In the present invention, a myosin inhibitor may be used to promote melanin accumulation and new hair growth in the induration zone, significantly reduce the accumulation of mesenchymal fibers, and promote the number of hair follicles or glands. In the present invention, a myosin inhibitor may be used to promote the proliferation of hair follicle cells, thereby promoting the formation of hair follicle. Further, in the present invention, a myosin inhibitor may be used to treat scleroderma.

In the present invention, a myosin inhibitor may be used to upregulate the expression of a gene associated with a general stress response, and may significantly upregulate a gene associated with initiation of regeneration, such as FST and a gene associated with neurogenesis.

In the present invention, a myosin inhibitor may be used to significantly upregulate the expression of a gene associated with DNA replication, homologous recombination, mismatch repair, nucleotide excision repair, or base excision repair.

EXAMPLES

The embodiments of the present invention are exemplified and described in detail below by way of specific examples. However, the following should not be construed as limiting the invention. The substances and the like used in the examples are all commercially available unless otherwise indicated.

Example 1: Destroying the Homeostasis of Cellular Mechanical System and Inducing Cell Softening by Using a Myosin Inhibitor FIG. 1A is a schematic diagram of laser confocal scanning. FIG. 1B shows respective treatment of human fibroblasts with DMSO (control) and (−)-blebbistatin (also referred to as Ble) (20 µM), staining by phalloidin; cells in the control group (the upper panels) have abundant stress fibers arranged in parallel, and the edge of a nucleus is smooth and round or elliptical; in the experimental group, the stress fibers in the cell are disintegrated after treatment with Ble, and the nucleus has irregular folds. FIG. 1C shows that nuclear lamina protein A/C has a strong uniform distribution around the DNA with an apparent polarity in the direction of the Basal-Apical, and the nuclear lamina protein A/C in the apical part is significantly higher than that in the basal part. The heterochromatin HP1 proteins show that the control group is significantly stronger than the experimental group. The results of FIG. 1D show that, the signal of nuclear localization of stress effect protein YAP1/TAZ is stronger than that of cytoplasmic localization in more than 90% of the cells in the experimental group, while only 35% of the cells in the experimental group after drug treatment have obvious nuclear localization. FIG. 1E: with quantitative PCR determination, proteins related to regulation of cellular mechanical hardness are significantly down-regulated after small molecule treatment. The ribosome transcriptional RNA is labeled with fluorouridine, as shown in FIG. 1F, the transcriptional active region of the control group is mainly concentrated near the center of the nucleus, and the experimental group shows that the active transcriptional region labeled with fluorouridine is also distributed near the periphery of the nucleus; three biological replicates. The effect of Bleb on epigenetics is determined by immunofluorescence staining, and as shown in FIG. 1G the results show that Bleb significantly reduced the modification of H3K27 trimethylation on day 4, and it is found through further verification of the component EZH2 of H3K27 trimethylation modified complex that, EZH2 is apparently localized at the nucleus in the control group, and the EZH2 protein level is down-regulated and it is localized at the cytoplasm in the Ble treatment group, as shown in FIG. 1H.

Example 2: Application of Inhibiting Hepatic Fibrosis Through Cell Softening in the Treatment of Hepatic Fibrosis-Related Diseases Hepatic fibrosis is an abnormal proliferation of connective tissue in the liver caused by various physiological and pathogenic factors in the pathophysiological process, accompanying with a large amount of extracellular matrix accumulation in liver tissue. Any type of liver damage is accompanied with varying degrees of hepatic fibrosis during liver repair and healing. If the damage factor cannot be removed for a long time, it will not only affect liver regeneration and normal liver function, but also develop into liver cirrhosis and even liver cancer due to a long term process of fibrosis. Anti-fibrosis treatment mainly includes: removal of pathogenic factors for primary disease, such as anti-hepatitis virus treatment, anti-parasitic (such as schistosomiasis) treatment, alcohol withdrawal and good living habits. The fibrosis itself may be treated by inhibiting inflammation, lipid peroxidation, or inhibiting the proliferation and activation of hepatic stellate cells, and promoting collagen degradation, etc. However, there is currently no safe and effective means for treating and preventing hepatic fibrosis in clinical practice. Therefore, it is urgent to find and develop new anti-fibrotic targets and their regulation means. The inventors of the present application find that, inhibition of myosin may destroy the cytoskeletal homeostasis, thereby softening cells, and the small molecule inhibitor of myosin, (−)-blebbistatin (abbreviated as Ble, Bleb or Blebb) is verified to have the effect of anti-fibrosis and promotion of regeneration and repair in a variety of liver damage models.

Figure 2:
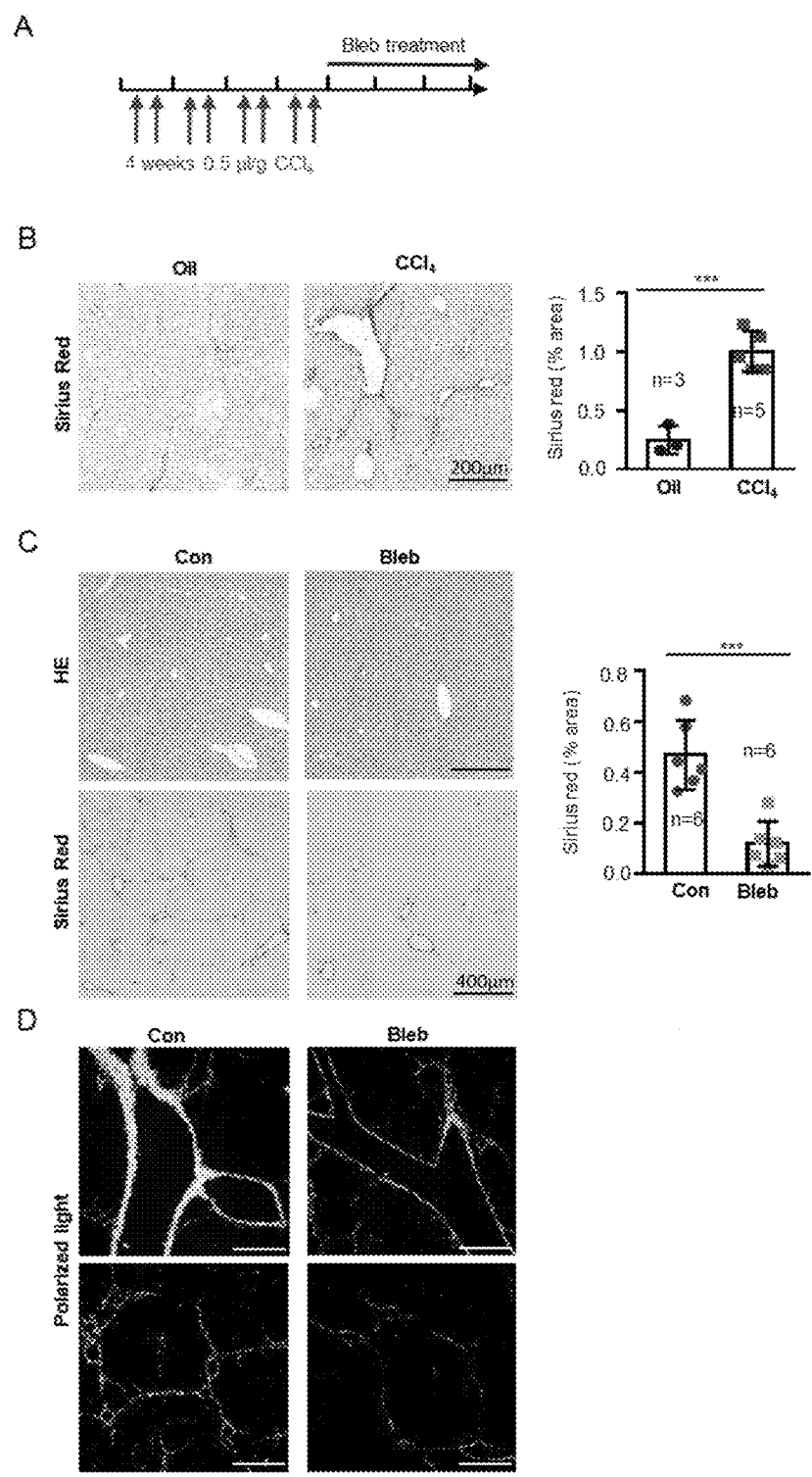
FIG. 2 shows the application of cell softening in inhibiting $CCl_4$-induced mild hepatic fibrosis, and the application of myosin inhibitor-induced stress response to inhibit fibrosis and promote regeneration repair in the repair of $CCl_4$-induced mild liver damage.

Example 2-1: Application of Cell Softening in Inhibiting $CCl_4$-Induced Mild Hepatic Fibrosis The ICR, C57Bl/6 mice used in the experiment are purchased from SPF (Beijing) Biotechnology Co., Ltd., carbon tetrachloride is purchased from Aladdin Reagent (Shanghai) Co., Ltd. (C131583-1L), and corn oil is purchased from Sigma (C8267). The experimental procedure of mild liver damage with $CCl_4$ is shown in FIG. 2A. 8-week-old female mice are selected and housed in the barrier for one week, they are randomly divided into two groups, and respectively injected with $CCl_4$/corn oil (a volume ratio of 2:5) and corn oil. The dose of $CCl_4$ is 0.5 ml/kg, twice a week for 4 weeks. After 4 weeks, the mice are anesthetized with 5% chloral hydrate, and part of the hepatic lobe is taken out, fixing with 4% paraformaldehyde, dehydrating and immersing in wax, then staining with Sirius Red (YY-R20384-100ML) kit for fibrosis, wherein the collagenous fibers are red, as shown in FIG. 2B. After successful identification of the modeling, the drug administration is performed by intraperitoneal injection or tail vein injection. The small molecule is dissolved in dimethyl sulfoxide at a concentration of 1 mg or 3 mg per kg per day; successfully adding 2-5% DMSO+30% propylene glycol+2% Tween 80+dd$H_2O$, and the control group ("Control") is abbreviated as "Con" in the figure. The intraperitoneal injection method is as follows: sucking the drug solution with a 1 ml syringe, puncturing the skin and abdominal wall muscle with a hypodermic syringe, and injecting the liquid into the abdominal cavity; taking care not to injure the diaphragm and other organs, and then staying for a while before withdrawing the needle to avoid liquid leakage. The method for injecting the tail vein is as follows: fixing the mouse in the holder, tightening the tail straightly, and stopping the bleeding with cotton after the injection. The injection is stopped after continuous injection for 1-2 weeks. The identification is performed again with Sirius red staining, and the results are shown in FIGS. 2C and 2D, the myosin inhibitor (−)-blebbistatin significantly inhibits fibrosis. It can be seen from the above experiment that the stress response induced by the myosin inhibitor inhibits fibrosis and promotes regeneration and repair in the repair of $CCl_4$-induced mild liver damage.

Figure 3:
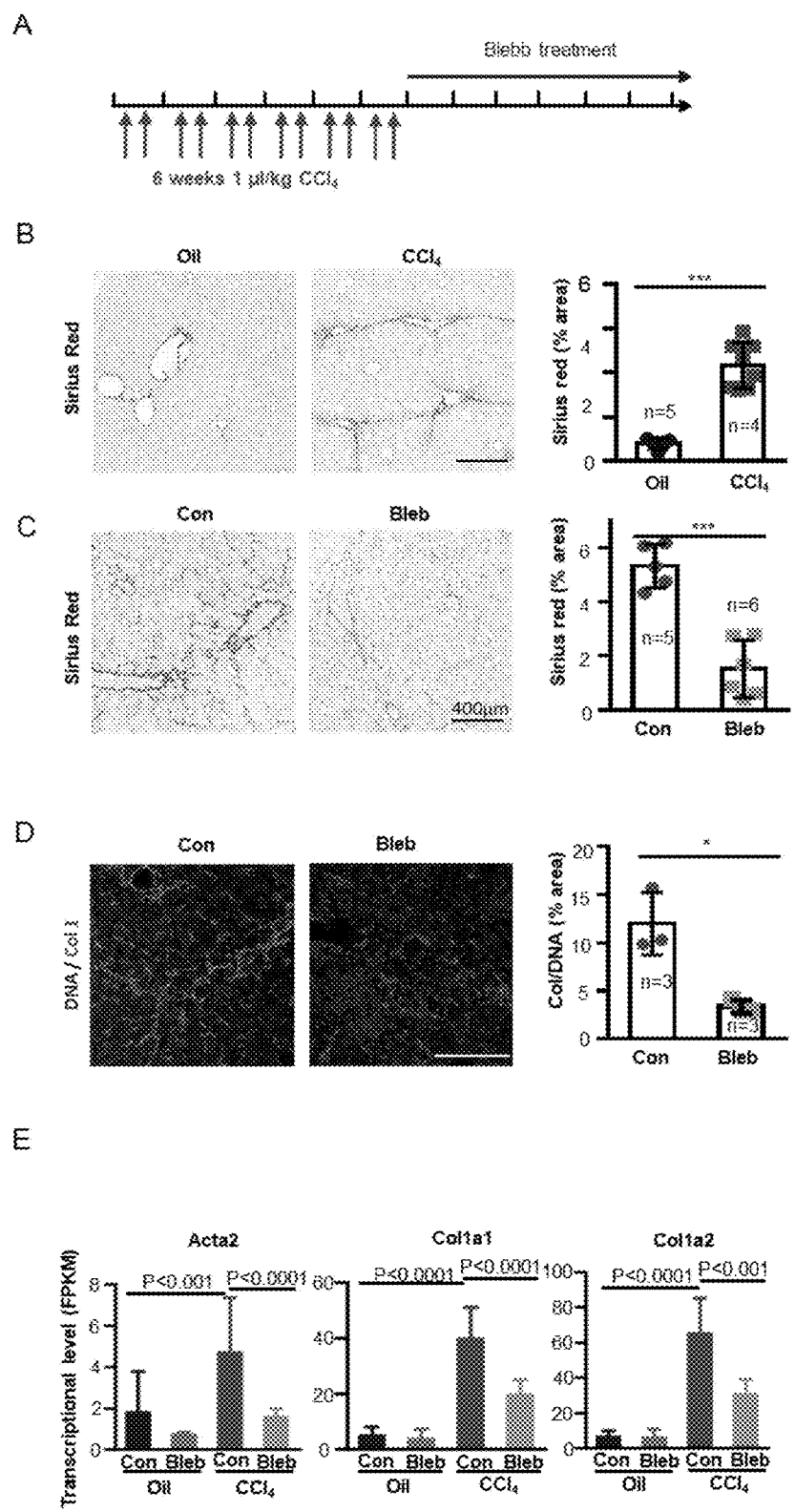
FIG. 3 shows the application of cell softening in inhibiting $CCl_4$-induced chronic severe hepatic fibrosis, and the application of myosin inhibitor-induced stress response to inhibit fibrosis and promote regeneration repair in the repair of $CCl_4$-induced chronic severe liver damage.
Figure 3:
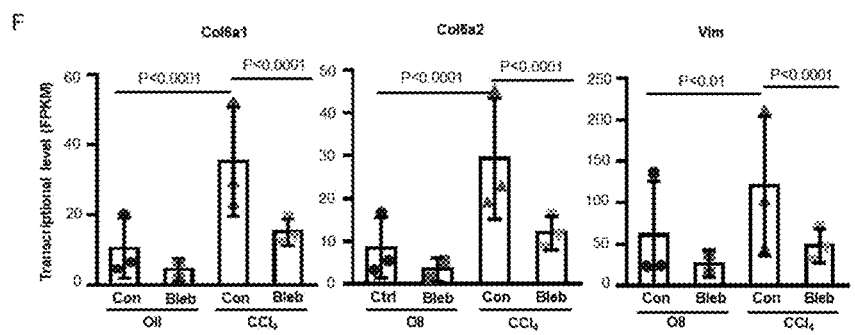

Example 2-2: Application of Cell Softening in Inhibiting $CCl_4$-Induced Chronic Severe Hepatic Fibrosis The ICR, C57Bl/6 mice used in the experiment are purchased from SPF (Beijing) Biotechnology Co., Ltd., carbon tetrachloride is purchased from Aladdin Reagent (Shanghai) Co., Ltd. (C131583-1L), and corn oil is purchased from Sigma (C8267). The experimental procedure of severe liver damage with $CCl_4$ is shown in FIG. 3A. 8-10 week-old female mice are selected and housed in the barrier for one week, they are randomly divided into two groups, and respectively injected with $CCl_4$/corn oil (a volume ratio of 1:2) and corn oil. The dose of $CCl_4$ is 2 ml/kg, twice a week for 4 weeks. After 6 weeks, the mice are anesthetized with 5% chloral hydrate, and part of the hepatic lobe is taken out, fixing with 4% paraformaldehyde, dehydrating and immersing in wax, then staining with Sirius Red (YY-R20384-100ML) kit for fibrosis, wherein the collagenous fibers are red, as shown in FIG. 3B. After successful identification of the modeling, the drug administration is performed by intraperitoneal injection or tail vein injection. The small molecule is dissolved in dimethyl sulfoxide at a concentration of 1 mg or 3 mg per kg per day; successfully adding 2-5% DMSO+30% propylene glycol+2% Tween 80+dd$H_2O$, and the control group ("Control") is abbreviated as "Con" in the figure. The intraperitoneal injection method is as follows: sucking the drug solution with a 1 ml syringe, puncturing the skin and abdominal wall muscle with a hypodermic syringe, and injecting the liquid into the abdominal cavity; taking care not to injure the diaphragm and other organs, and then staying for a while before withdrawing the needle to avoid liquid leakage. The method for injecting the tail vein is as follows: fixing the mouse in the holder, tightening the tail straightly, and stopping the bleeding with cotton after the injection. The injection is stopped after continuous injection for 6-8 weeks. The identification is performed again with Sirius red staining (for identification of collagenous fibers), and the results are shown in FIG. 3C, and the results of type I collagen Col I staining are shown in FIG. 3D. Further, quantitative PCR is performed to identify the expression of fibrosis-related genes Acta2 (myofibroblast marker), Col1a1 (representing type I collagen), Col1a2 (representing type I collagen), Col6a1 (representing collagen), Col6a2 (representing collagen), and Vim (representing fibroblasts), as shown in FIG. 3E and FIG. 3F (continued). The myosin inhibitor (−)-blebbistatin inhibits the accumulation of collagenous fibers and the activation of myofibroblasts during the process of chronic severe liver damage induced by $CCl_4$, thereby inhibiting fibrosis of tissues. Meanwhile, it can be seen that the stress response induced by the myosin inhibitor inhibits fibrosis and promotes regeneration and repair in the repair of CCl$_4$-induced chronic severe liver damage.

Figure 4:
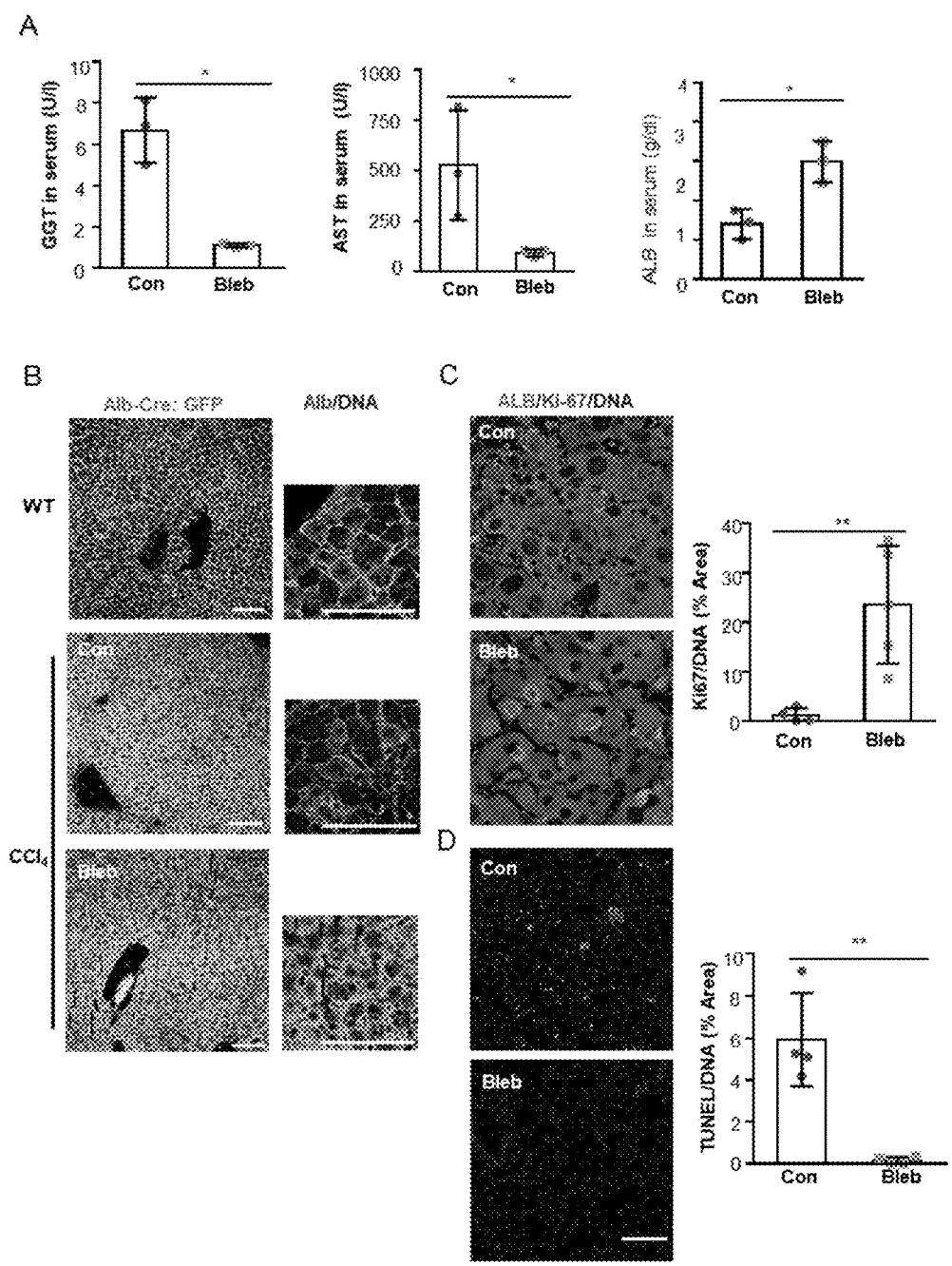
FIG. 4 shows that cell softening inhibits tissue fibrosis, promotes hepatocyte proliferation, and promotes liver regeneration; and the stress response induced by a myosin inhibitor also inhibits tissue fibrosis, promotes hepatocyte proliferation, and promotes liver regeneration.
Figure 4E:
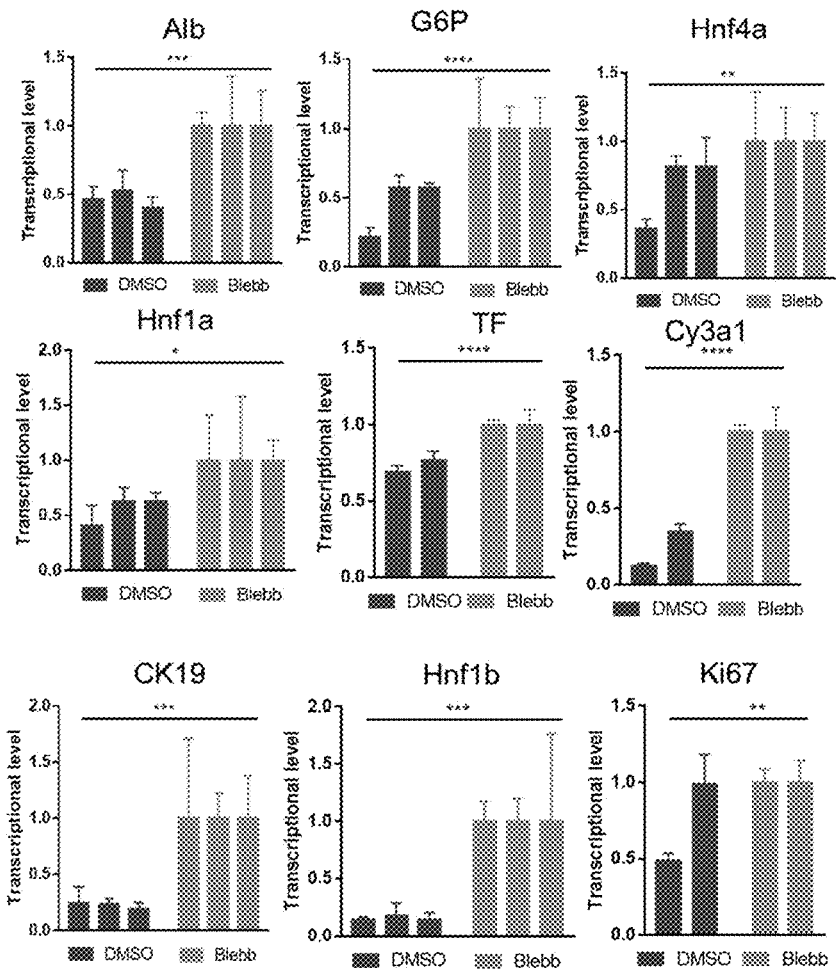
FIG. 4E shows the transcription level quantitation of indicators related to liver function in liver tissue in the treatment group and control group (n=3 mice per group). Data are expressed as mean±SD. *$P<0.05$, $P<0.01$, *$P<0.001$.

Example 2-3: Application of Cell Softening in Inhibiting Tissue Fibrosis, Promoting hepatocyte proliferation, and promoting liver regeneration Blood biochemical analysis (fasting 12-16 hours before sampling) further confirms that myosin inhibitor (−)-blebbistatin may reduce the content of liver damage indicators such as ALT, AST and GGT, as shown in FIG. 4A. Further, Alb-crexmTmG hybrid mice are used for fibrosis modeling with CCl$_4$, wherein GFP is expressed in mature hepatocytes of the mice. After drug treatment, most of the cells expressing GFP express Alb; while for cells treated with DMSO, part of the cells expressing GFP do not express Alb; indicating that the myosin inhibitor (−)-blebbistatin may prevent loss of liver function during liver damage, as shown in FIG. 4B. Further, it is confirmed by staining that (−)-blebbistatin significantly promotes cell proliferation after liver damage, as shown in FIG. 4C; and reduces apoptosis during liver damage, as shown in FIG. 4D. Further, it is found by transcriptional level analysis of liver function-related indicators that, as compared with the control group, the treatment of myosin inhibitor (−)-blebbistatin significantly maintains high level expression of hepatocyte-related genes (Alb, G6P, Hnf4a, Hnf1a, TF, Cy3a1), and bile duct-related genes (CK19, Hnf1b), and proliferation-related genes (Ki67), as shown in FIG. 4E (continued). In summary, the myosin inhibitor (−)-blebbistatin promotes liver regeneration by inhibiting fibrosis of liver damage, promoting hepatocyte proliferation, and reducing apoptosis, thereby maintaining liver function. It can also be seen from the above results that, the stress response induced by the myosin inhibitor inhibits tissue fibrosis, promotes hepatocyte proliferation, and promotes liver regeneration.

Figure 5:
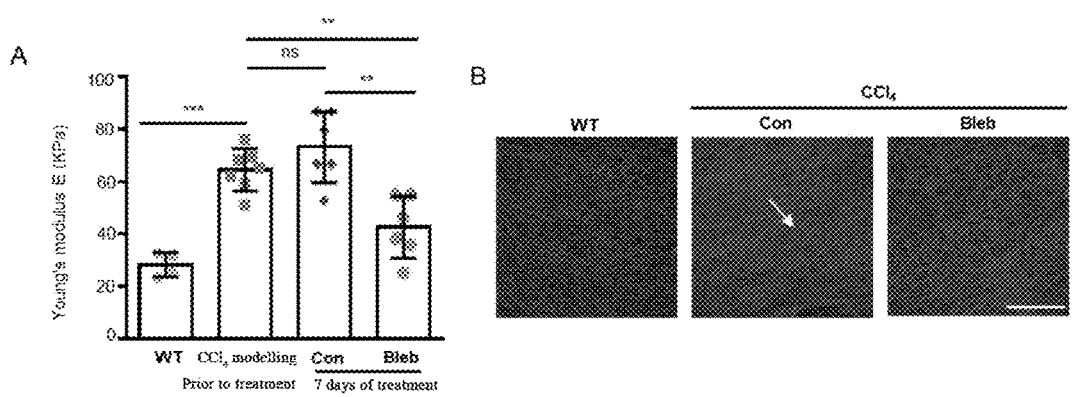
FIG. 5 shows the application of cell softening to reduce tissue and organ sclerosis during liver damage, and myosin inhibitor reduces tissue rigidity during liver damage.
Figure 6:
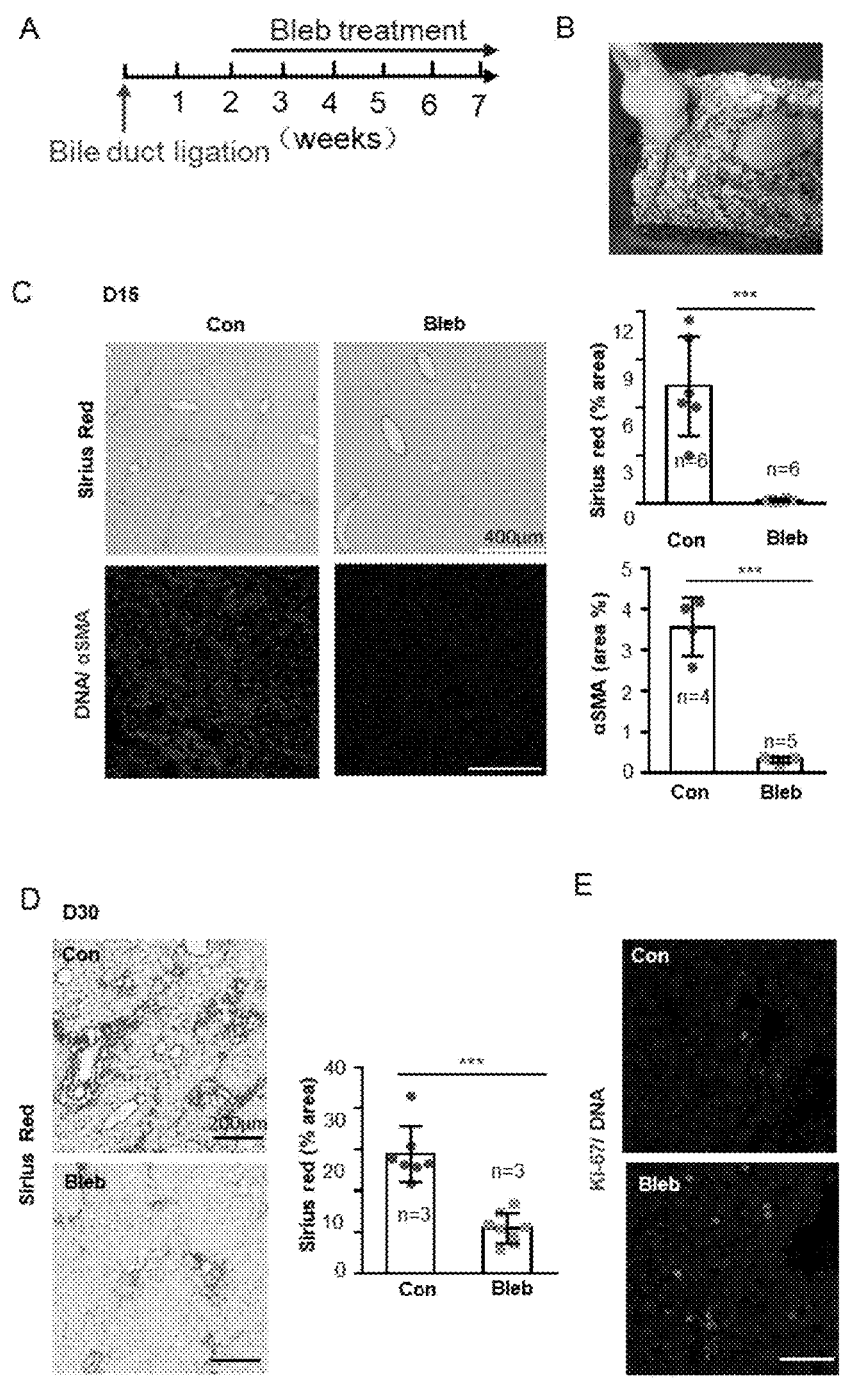
FIG. 6 shows the application of cell softening in inhibiting hepatic fibrosis induced by bile duct ligation, and the application of stress response induced by a myosin inhibitor in hepatic injury of bile duct ligation.

Example 2-4: Application of Cell Softening in Reducing Tissue and Organ Damage During Liver Damage The ICR, C57B1/6 mice used in the experiment are purchased from SPF (Beijing) Biotechnology Co., Ltd.; elbow tweezers, finger tweezers, scissors, needle holders, suture needles, suture threads are purchased from Asone Trading Co., Ltd.; antibiotics are purchased from Gibco (15240-062). A chronic severe liver damage model induced by CCl$_4$ (the same as Example 4) is constructed, and the mice are sacrificed by cervical dislocation after modeling. The Young's modulus of fresh liver tissue is detected by Mark-10 ESM303; as compared with non-modeling group, the Young's modulus of liver tissue of the liver in CCl$_4$-modeling group is significantly increased (as shown in FIG. 6A, "WT" and "CCl$_4$-modeling"). The mice of successful modeling are evenly divided into two groups, and respectively treated with DMSO ("Con" in the figure) and (−)-blebbistatin; after 7 days of treatment, the mice are sacrificed by cervical dislocation, and the Young's modulus of fresh liver tissue is detected by Mark-10 ESM303; the results show that myosin significantly reduces the rigidity of liver tissue on day 7 of the treatment, as shown in FIG. 5A, "7 days of treatment-Con" and "7 days of treatment-Bleb". Meanwhile, the results of the second harmonic intravital scanning show that, the massive parallel array of fibers in the liver tissue (FIG. 5B, indicated by the arrow in the middle panel) is reduced in the (−)-blebbistatin treatment group (FIG. 5B right panel), presenting a grid structure closer to normal mice. It can be seen from the above results that, the myosin inhibitor reduces the tissue rigidity during liver damage process.

Example 2-5: Application of Cell Softening in Inhibiting Bile Duct Ligation-Induced Fibrosis The ICR, C57B1/6 mice used in the experiment are purchased from SPF (Beijing) Biotechnology Co., Ltd.; elbow tweezers, finger tweezers, scissors, needle holders, suture needles, suture threads are purchased from Asone Trading Co., Ltd.; antibiotics are purchased from Gibco (15240-062).

8 week-old female mice are used, and they are fasted for 24 hours before the experiment. The mice are anesthetized with 5% chloral hydrate, and intraperitoneally injected with 8 ml/kg. The mice are fixed after anesthesia, and an incision is made in the abdomen to expose the organs. The duodenum of the stomach end is found and gently pulled to find the bile duct, carefully peeling off the bile duct with tweezers, ligating the bile duct with suture thread, then adding antibiotics, and suturing to close the abdominal cavity. The mice are fasted for 12 hours after surgery.

14-20 days after surgery, the skin of the mice is observed to be yellow-green, and drug is administered to mice for treatment. The mice in the modeling group are evenly divided into two groups, and the mice of experimental group are intraperitoneally injected with (−)-blebbistatin. As for the administration method, (−)-blebbistatin is dissolved in DMSO; sequentially adding 2-5% DMSO (final concentration, volume ratio)+30% PEG400 (final concentration, volume ratio)+2% Tween 80 (final concentration, volume ratio), the mice of the control group are injected with a solvent without the small molecule but containing an equal amount of DMSO (denoted as "Con").

FIG. 6A shows a flow diagram of the experiment about the treatment of fibrosis of liver damage caused by bile duct ligation with (−)-blebbistatin (hereinafter abbreviated as Bleb). Results: FIG. 6B shows that the dimethyl sulfoxide-treated mice in the hepatic fibrosis model control group are wilting and have decreased activity; on the contrary, the group of mice treated with myosin inhibitor Bleb significantly inhibited treatment are more active and energetic. FIG. 6C: Sirius Red and α-SMA staining results show that, after 15 days of treatment with myosin inhibitor (−)-blebbistatin, the accumulation of collagenous fibers (the upper panels of FIG. 6C) and proliferation of myofibroblasts (the lower panels of FIG. 6C) caused by bile duct ligation are significantly inhibited. After 30 days of treatment, as compared with the control group (representing with "Control", which is abbreviated as "Con" in the figure), Bleb still significantly inhibits the accumulation of collagenous fibers caused by bile duct ligation (FIG. 6D). The staining of cell proliferation protein Ki-67 shows that, Bleb promotes hepatocyte proliferation during the bile duct ligation process (FIG. 6E).

The above results show the application of stress response induced by the myosin inhibitor in treating liver damage of bile duct ligation.

Figure 7:
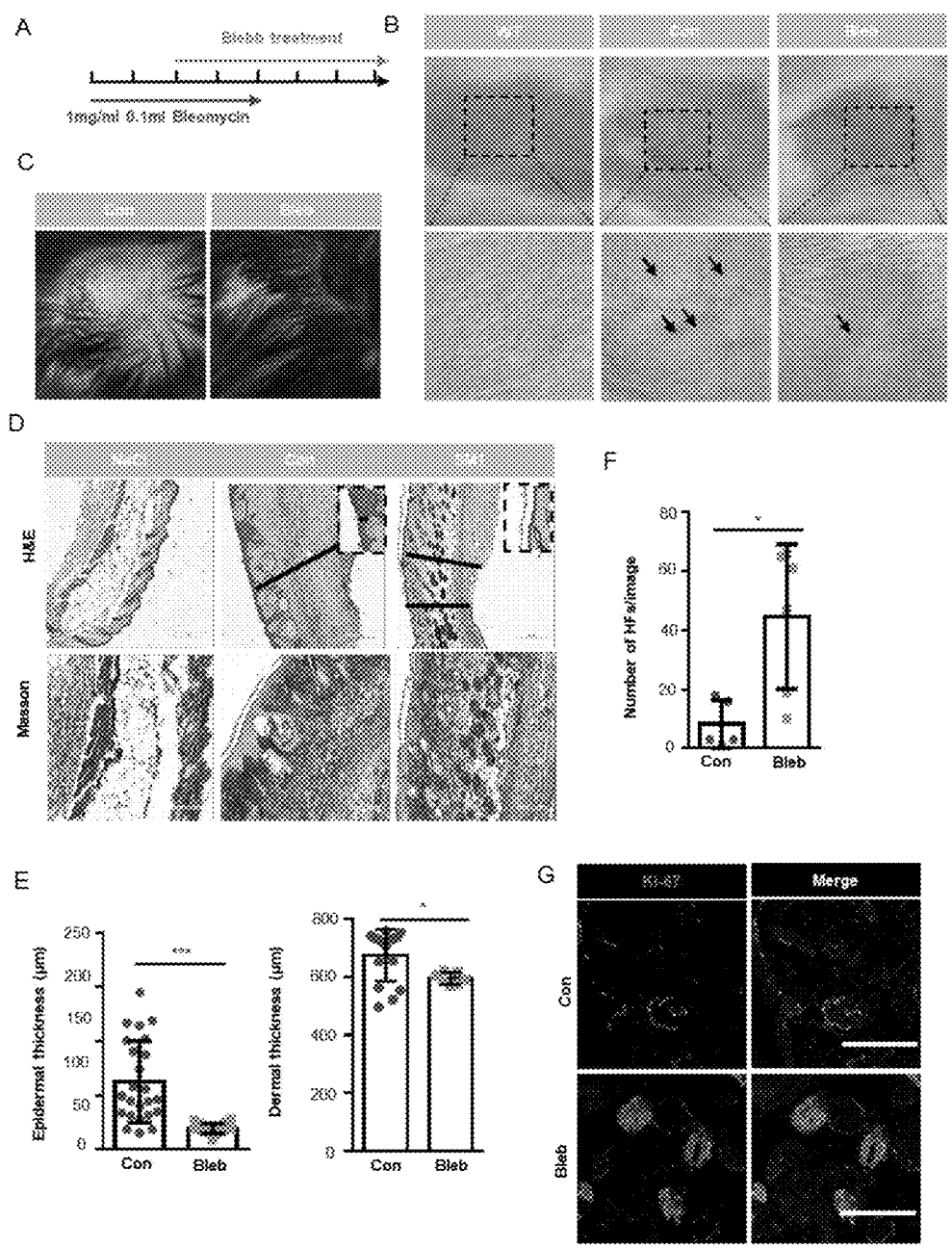
FIG. 7 shows the application of cell softening in inhibiting skin fibrosis and the treatment of scleroderma, and the application of stress response induced by myosin inhibitor in the treatment of scleroderma.
Figure 7:
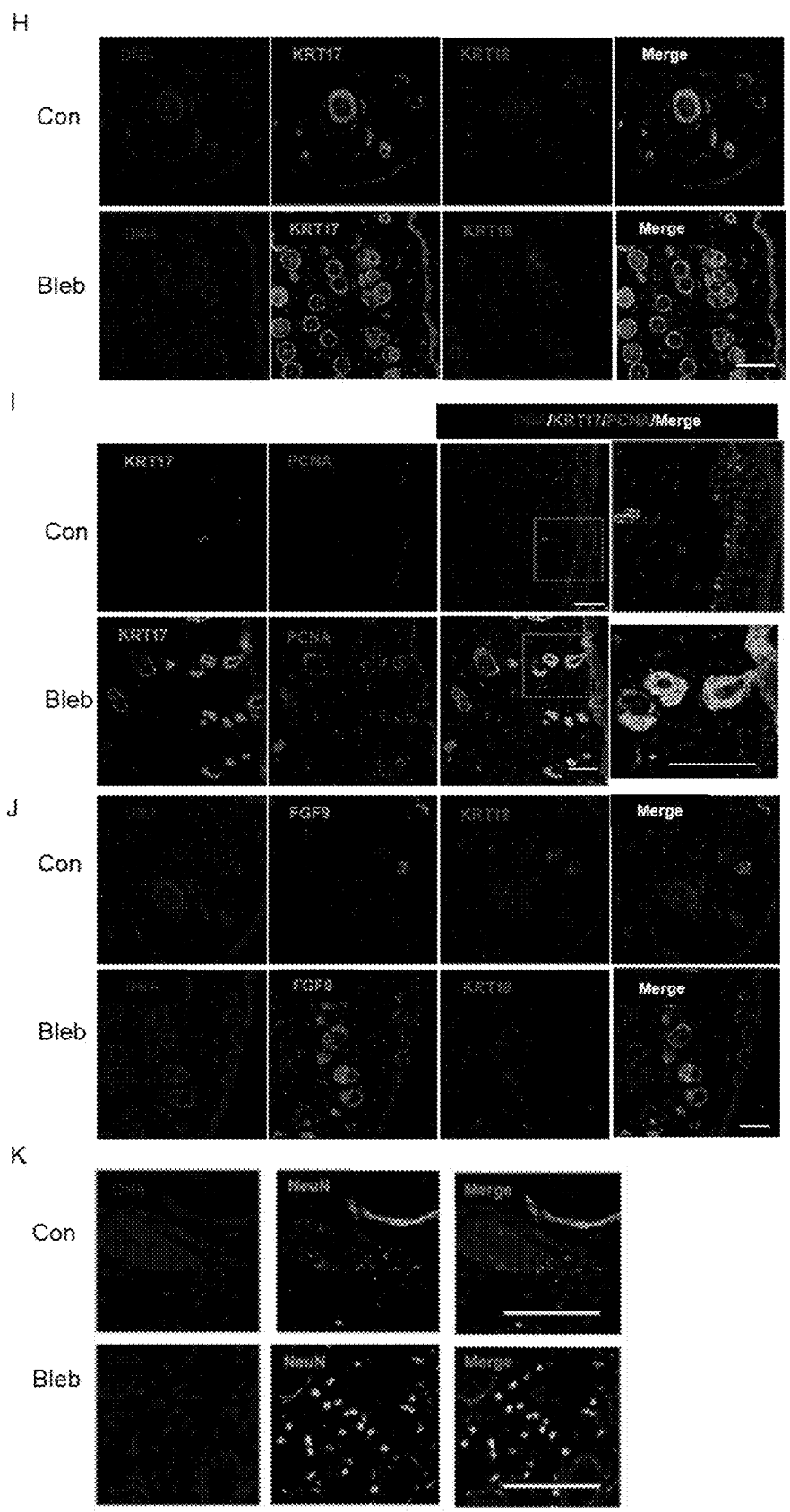

Example 3: Application of Inhibiting Skin Fibrosis Through Cell Softening in the Treatment of Scleroderma Scleroderma is a connective tissue disease characterized by localized or diffuse fibrosis of the skin and internal organs, thereby hardening and shrinking. The disease may cause multisystem injury, its exact cause and pathogenesis are still unclear, and there is no effective treatment means. In the present invention, bleomycin (BLM) locally injected on the back of ICR or C57Bl/6 mice, and skin sclerosis in mice is successfully induced; the mice are treated by intraperitoneal administration of myosin inhibitor (−)-blebbistatin, and the experimental procedure is shown in FIG. 7A.

One week after injection of bleomycin, the skin at the injection site on the back of mice begins to thicken and harden, and has poor elasticity; there is no change in hair growth until the end of the injection; meanwhile, induration and incrustation occurs at the injection site, accompanying with superficial ulcers. As for the shaved injection area on the back of the mice in the saline control group, the hair grows continuously, and no significant skin hardening and thickening phenomenon is observed, as shown in FIG. 7B. Treatment group (Bleb): intraperitoneal administration of myosin inhibitor (−)-blebbistatin (1-3 mg/kg/day, dissolved in 2-5% DMSO+30% PEG400+2% Tween 80+ddH$_2$O); control group (con): without (−)-blebbistatin but containing the same amount of DMSO. After 3 weeks of treatment, the degree of induration and incrustation is significantly reduced in the treatment group, accompanying with lesser degree of superficial ulcer, as shown in FIG. 7B. Further experiments confirm that the myosin inhibitor (−)-blebbistatin promotes melanin accumulation in the induration zone and the growth of new hair, as shown in FIG. 7C. The results of H&E and Massion fiber staining show that, (−)-blebbistatin significantly reduces the accumulation of mesenchymal fibers, as indicated in FIG. 7D. Further analysis shows that (−)-blebbistatin treatment significantly reduces epidermal and dermal thickness (as shown in FIG. 7E), and promotes the number of hair follicles or glands (as shown in FIG. 8F). The results of Ki-67 staining show that (−)-blebbistatin promotes hair follicle cell proliferation, thereby promoting hair follicle formation, as shown in FIG. 7G. Further, after identification by immunostaining, the KRT17 (hair follicle marker protein) positive cells in the (−)-blebbistatin treatment group are much more than the KRT18 (glandular marker protein) positive cells, as shown in FIG. 7H (continued); through co-immunostaining KRT17 and proliferation marker protein PCNA, it is found that (−)-blebbistatin promotes hair follicle regeneration by promoting hair follicle cell proliferation, as shown in FIG. 7I (continued). It is further found that more FGF9 is expressed in the (−)-blebbistatin treatment group, which is reported to promote hair follicle regeneration, as shown in FIG. 7J (continued). Surprisingly, (−)-blebbistatin promotes the appearance of neural fate in the induration zone, and marker NeuN of nuclear-localized mature neurons is expressed in some cells after (−)-blebbistatin treatment, as shown in FIG. 7K, suggesting whether the appearance of induced neural fate is useful for damage repair and tissue regeneration needs further research. The above results show the application of the stress response induced by myosin inhibitor in the treatment of scleroderma.

Example 4: Application of Inhibiting Pulmonary Fibrosis Through Cell Softening in the Treatment of Pulmonary Fibrosis-Related Diseases Pulmonary fibrosis is a pathological change characterized by fibroblast proliferation, a large amount of extracellular matrix accumulation accompanied with inflammatory damage and destruction of tissue structure; i.e., a structural abnormality (scar formation) caused by abnormal repair of the damaged normal alveolar tissue. Pulmonary fibrosis will seriously affect the respiratory function of human body, the clinical manifestations are various types of dyspnea, and the respiratory function of the patient will get worse with the aggravation of the disease and lung damage. It is reported that the morbidity and mortality of idiopathic pulmonary fibrosis has increased worldwide year by year, and the average survival time after diagnosis is less than 3 years, and is higher than most tumors, so it is also called a "tumor-like disease". Therefore, it has important application value in the treatment and prevention of pulmonary fibrosis-related diseases to find new targets and drugs that may effectively inhibit pulmonary fibrosis.

In the invention, bleomycin (BLM) is instilled into pulmonary tracheal of ICR or C57Bl/6 mice to successfully construct a mouse model of pulmonary fibrosis, and the mice are treated by intraperitoneal administration of myosin inhibitor (−)-blebbistatin. It is proved that (−)-blebbistatin has the effect of inhibiting pulmonary fibrosis and significantly promoting survival in mice with pulmonary fibrosis. The specific experimental procedure is shown in FIG. 8A. The detailed processes of injecting bleomycin are as follows:

(1) Dilution of bleomycin: 50 mg/ml stock solution is diluted 25 times to obtain a final concentration of 2 mg/ml.

(2) The mice are anesthetized by intraperitoneal injection of 0.5% sodium pentobarbital (100 µl/10 g b.w.).

(3) The neck skin is disinfected by 75% alcohol, cutting the neck skin and bluntly separating the mucosa and muscles of the trachea, exposing the trachea, and taking care not to damage the thyroid.

(4) 50 µl (20 g body weight) of bleomycin is injected into the interval of tracheal cartilage by an insulin syringe at a dose of 5 mg/kg. After the needle is pulled out, putting the console upright, rotating left and right for 1 min, and then the skin is sutured. The mice eat food and drink water freely after spontaneously awakening.

Figure 8:
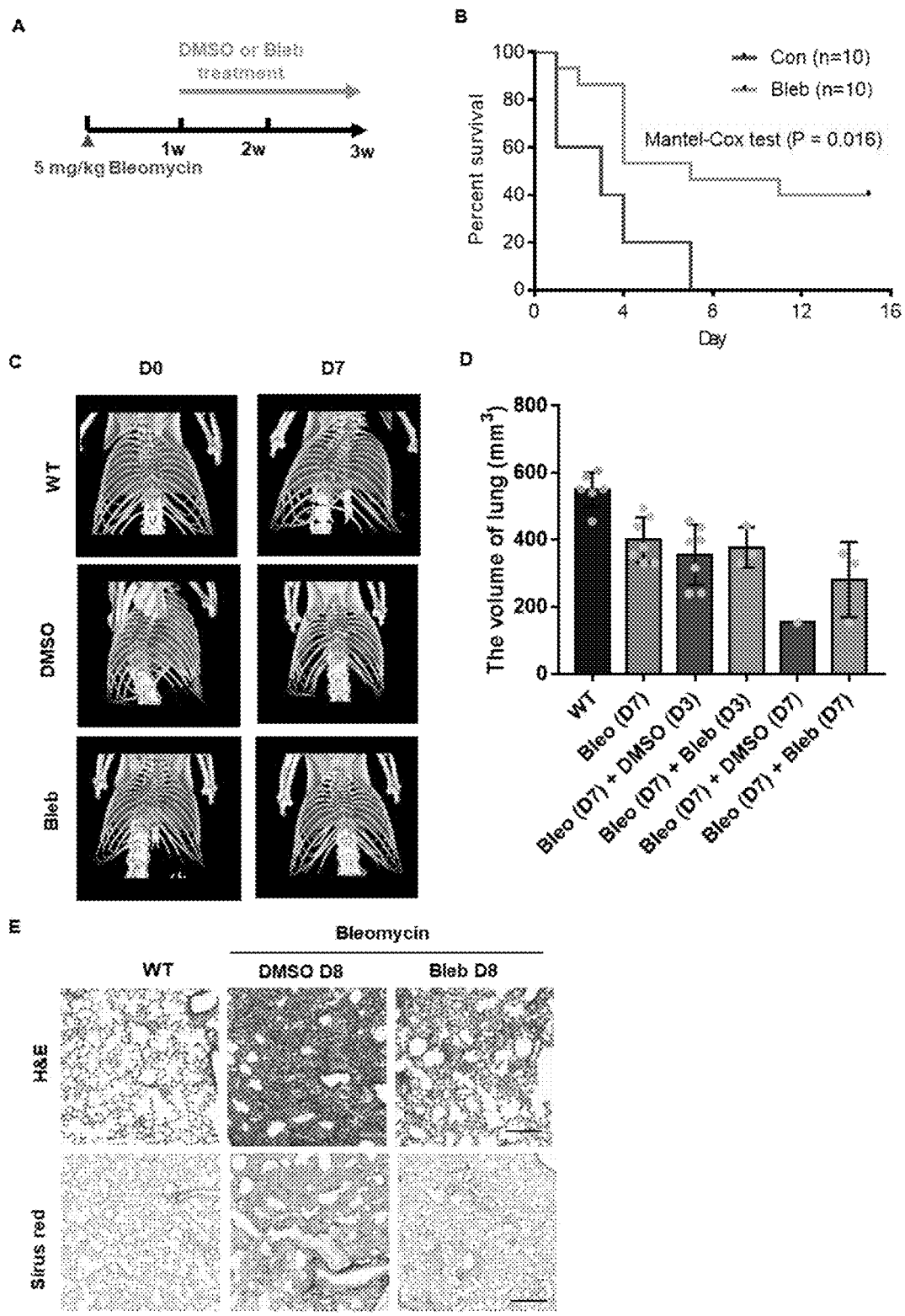
FIG. 8 shows the application of cell softening in inhibiting pulmonary fibrosis.

(5) Scanning is performed by small animal CT 7 days after surgery, and the results are shown in FIGS. 8C and 8D, (−)-blebbistatin inhibits the decrease in lung volume during bleomycin-induced lung damage. The mice are identified and divided into two groups: DMSO (indicated as "Con" in FIG. 8) and (−)-blebbistatin (indicated as "Bleb" in FIG. 8, 1-3 mg/kg/day) are respectively administrated by intraperitoneal injection, wherein they are respectively dissolved in 2-5% DMSO+30% PEG400+2% Tween80+ddH$_2$O. The survival status of the mice is recorded with intraperitoneal injection/day, tail vein injection/3 days. The result is shown in FIG. 8B, all the mice in the control group died on day 8 of treatment, while the mice in the Bleb treatment group have a survival rate of 40% on day 15 of treatment. Statistical analysis shows that (−)-blebbistatin significantly improves bleomycin-induced pulmonary fibrosis, 10 mice per group.

(6) Small animal CT scanning is performed on D8 (modeling on D14), the samples are taken and fixed after heart perfusion, slicing the samples and performing H&E and Sirius red staining. The result is shown in FIG. 8D, (−)-blebbistatin inhibits tissue damage and fibrosis during bleomycin-induced lung damage.

Figure 9A:
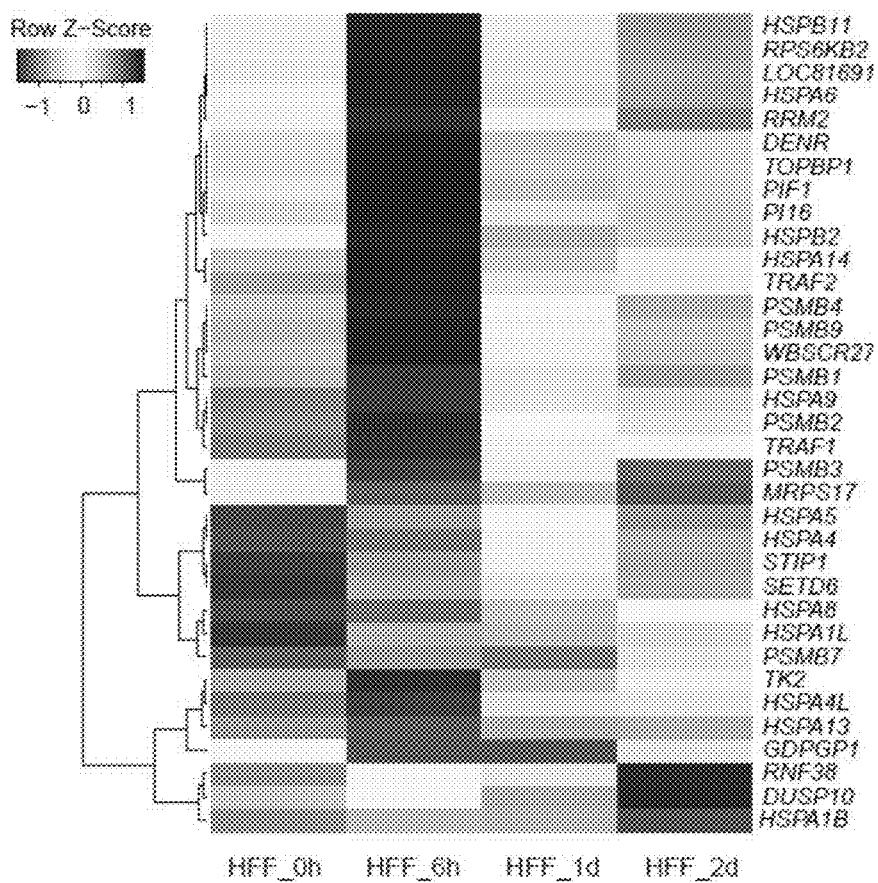
FIGS. 9(A)-(C) show that the myosin inhibitor destroys the steady state of cellular mechanical system, thereby destroying stress response associated with regeneration induction and responses associated with regeneration initiation and tissue genesis.
Figure 9B:
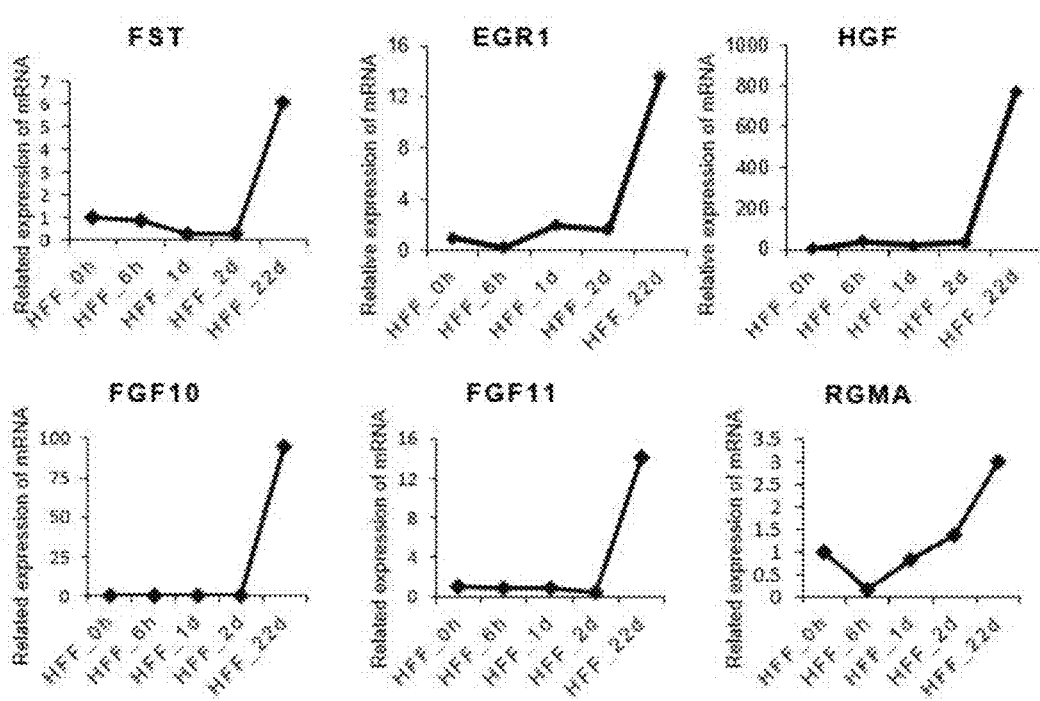
Figure 9C:
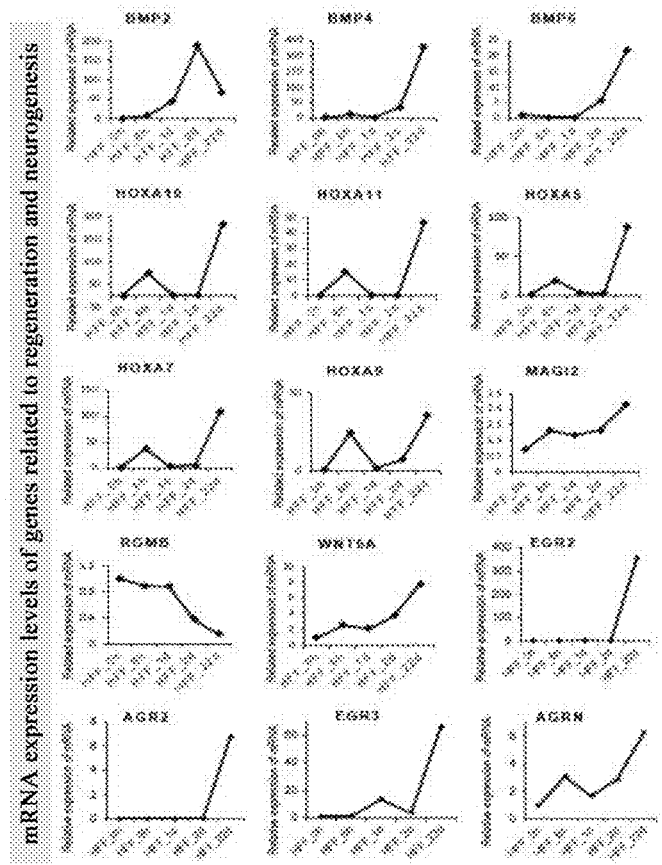

Example 5: Destruction of Homeostasis in Cell Mechanical System Induces Regeneration-Related Stress Response and Responses Related to Initiation of Regeneration and Histogenesis Human fibroblasts are treated with (−)-blebbistatin, and samples are respectively collected after treatment for 0 hour, 6 hours, 1 day, and 2 days for transcriptome sequencing, data analysis is shown in FIG. 9 (A), a large number of genes related to general stress response (such as HSP70 family and HSP90, etc.) are upregulated in early 6 hours of the induction. The mRNA expression of these genes begins to downregulate on day 1 and day 2. After induction for 22 days under the neural induction system, genes related to initiation of regeneration (such as FST) and neurogenesis-related genes are significantly upregulated, as shown in FIG. 9(B) and FIG. 9(C).

Figure 10A:
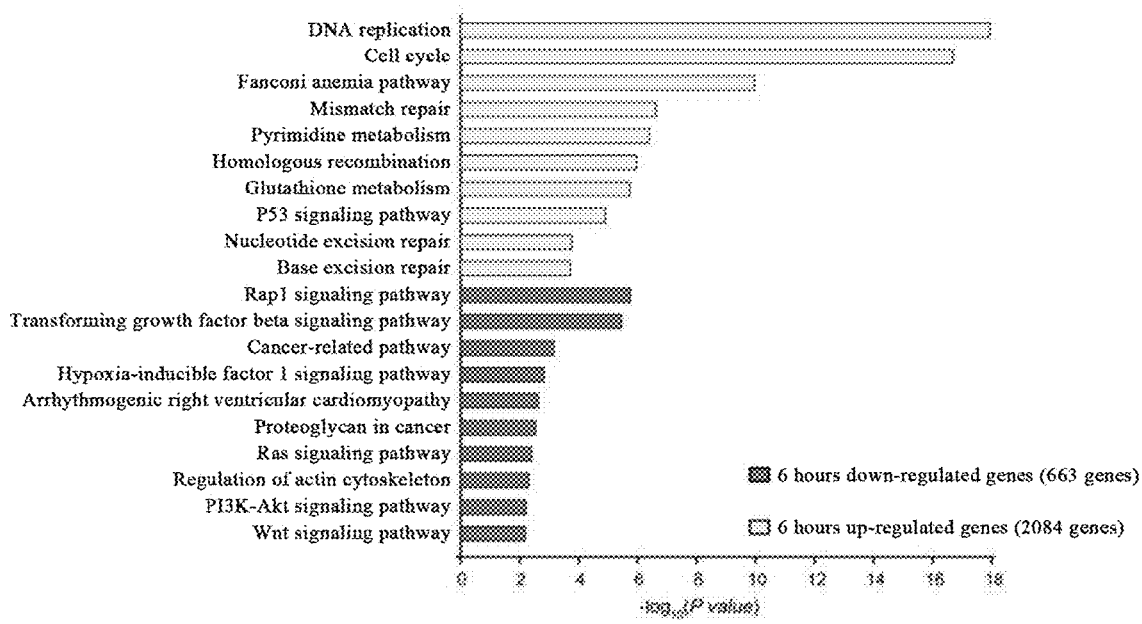
FIG. 10 shows that stress response stimulated by (−)-blebbistatin activates high genetic damage repair response, thereby improving the up-regulation of the homologous recombination repair gene in the body.
Figure 10B:
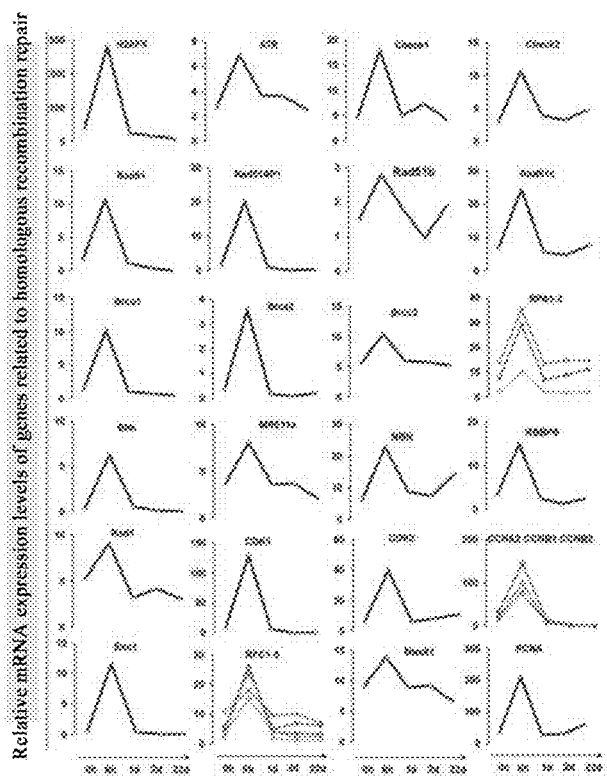

Example 6: (−)-Blebbistatin Stimulates High Genetic Damage Repair Response Activated by Stress Response, and Improves Upregulation of the Homologous Recombination Repair Gene in the Body As shown in FIG. 10A, human fibroblasts are treated with 5-50 μM (−)-blebbistatin, and transcriptome analysis after 6 hours shows that, DNA replication-related genes, homologous recombination-related genes, mismatch repair-related genes, nucleotide excision repair-related and base excision repair-related genes are significantly upregulated. As shown in FIG. 10B, further analysis reveals that almost all of the important genes involved in homologous recombination are significantly upregulated.

Figure 11A:
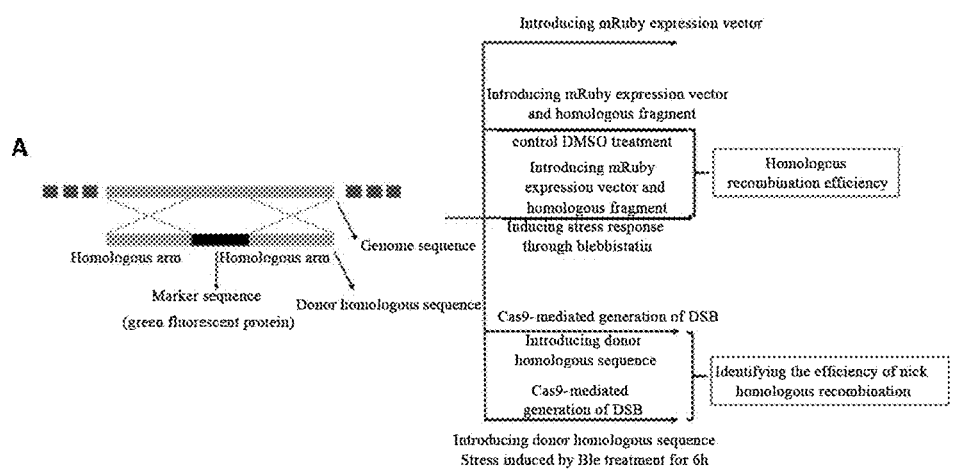

Example 7: The Application of Stimulating High Genetic Damage Repair Response Activated by Stress Response Through (−)-Blebbistatin in the Process of Improving Homologous Recombination Repair of Genes in the Body The experimental procedure is shown in FIG. 11A. First, a reporter plasmid system for homologous recombination repair is constructed, and the cells emit green fluorescence only when the foreign homologous sequence and the homologous fragment of the cell are homologously recombined. Meanwhile, mRuby red fluorescent protein is transferred to label the efficiency of transfected cells, and the efficiency of homologous recombination is determined by flow cytometry analysis of the ratio of green fluorescent protein to mRuby. 18 h after changing the medium for the transfection, the control group is treated with DMSO for 4 h; and 18 h, 24 h, and 36 h after changing the medium for the transfection, the experimental group is treated with (−)-blebbistatin for 4 h, and the HDR efficiency is analyzed by flow analysis 72 h after transfection. The results show that (−)-blebbistatin significantly increases the efficiency of homologous recombination in the body, as shown in FIGS. 11(B)-(C). Since Nrf2 is a gene significantly upregulated by oxidative stress, Nrf2 is also an effector protein of oxidative stress, small molecule Nrf activator is used to simulate oxidative stress so as to further verify that stress response may improve the ability of homologous recombination, as shown in FIGS. 11(D)-(E). The experimental procedure is as follows: after changing the medium for the transfection, the control group is treated with DMSO; and after changing the medium for the transfection, the experimental group is treated with 250 nM RTA408; then the HDR efficiency is analyzed by flow analysis 72 h after transfection.

Example 8: Application of Stimulating Stress Response Through Myosin Inhibitor in Promoting Amplification of Human Hepatocytes In Vitro Examples 1-6 show that stimulating stress response through myosin inhibitor may inhibit liver or skin fibrosis in different mouse models of liver damage or skin lesion, and promote proliferation of hepatocytes or hair follicle cells, thereby promoting regeneration of liver or hair follicles. This example further validates that the myosin inhibitor inhibits human hepatocyte fibrosis and promotes hepatocyte proliferation, and it provides further evidence for further application of this method in the treatment of human liver damage and related diseases.

Example 8-1: Culture of Human Embryonic Hepatocytes

Resuscitation of Human Embryonic Hepatocytes: human embryonic hepatocytes are removed from a liquid nitrogen tank (aborted fetus, frozen storage date is Jan. 15, 2014, frozen stock solution is cell banker 2, frozen cell number is $2 \times 10^7$/tube), quickly placing in a 37° C. water bath; and after melting the cells are immediately inhaled into a 15 ml centrifuge tube containing 5 ml of hepatocyte medium (control group), centrifuging at 50 g, 4° C. for 5 min; the supernatant is discarded, and the cells are resuspended in 500 ul hepatocyte medium and calculated as $1.16 \times 10^6$ with a cell recovery rate of 5.8%.

Inoculation of Human Embryonic Hepatocytes: inoculation density is $1 \times 10^5$/24 well plate, adding 500 μl hepatocyte medium (control group), hepatocyte medium containing 10 μM small molecules, and hepatocyte medium containing 20 μM small molecules respectively; 24 hours after inoculating, 3 wells of cells in each group are digested respectively to count the number of the cells, then calculating the cell adherent rate. 72 hours after inoculating, 3 wells of cells in each group are digested respectively to count the number of the cells. Multiple of the change of cell number may be obtained through dividing the number of cells at 72 hours after inoculation by the number of cells at 24 hours after inoculation. A portion of the cells per well (⅖ of the cell count) are taken for RNA extraction so as to detect human hepatocyte-related gene expression.

The First Passage of Human Embryonic Hepatocytes: cells are respectively inoculated into a 24-well plate coated with rat tail collagen (as described above), and the inoculum density is ⅗ of the number of cells after 72 hours of primary culture; 3 duplicate wells per group. After 72 hours of cell culture, the cells are digested to count the number. Multiple of the first passage amplification may be obtained through dividing the counted number of cells by the number of cells at the time of inoculation. A portion of the cells per well (⅖ of the cell count) are taken for RNA extraction so as to detect human hepatocyte-related gene expression.

The Second Passage of Human Embryonic Hepatocytes: cells are respectively inoculated into a 24-well plate coated with rat tail collagen (as described above), and the inoculum density is ⅗ of the number of cells after 72 hours of the first passage culture. Since most of the cells died after 72 hours of the first passage culture in the control group, only a small number of cells remained, so all of these cells are inoculated. After changing the medium every 2 days and continuing to culture for 144 hours (6 days), the cells are digested and counted. Multiple of the second passage amplification may be obtained through dividing the counted number of cells by the number of cells at the time of inoculation. Cell culture supernatants from each well are taken respectively to detect the concentration of human albumin, and a portion of the cells (⅖ of the cell count) are taken for RNA extraction so as to detect human hepatocyte-related gene expression.

Figure 12A:
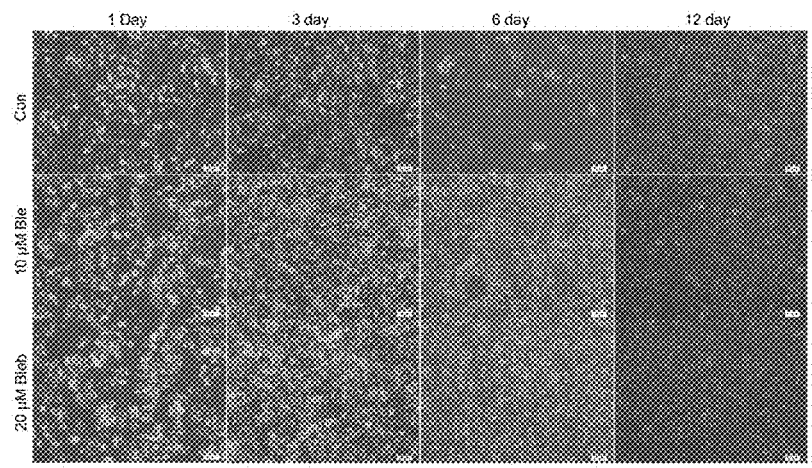
FIGS. 12(A)-(C) show the use of stress response stimulated by myosin inhibitor in promoting the amplification of human hepatocytes in vitro.
Figure 12B:
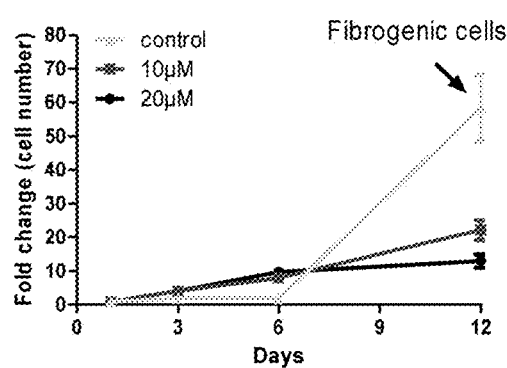
Figure 12C:
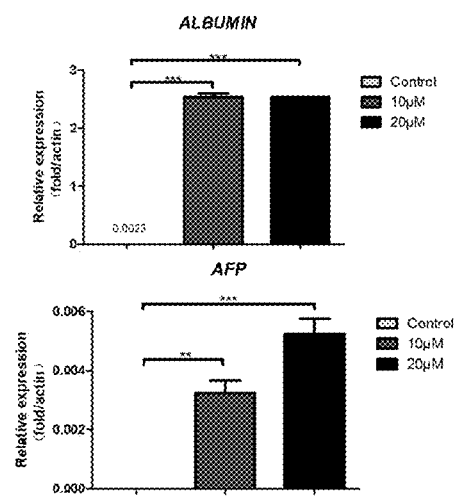
Figure 12D:
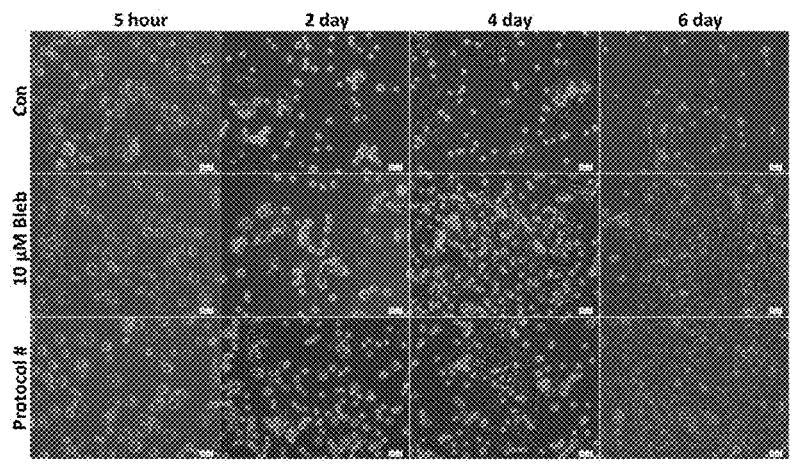
Figure 12E:
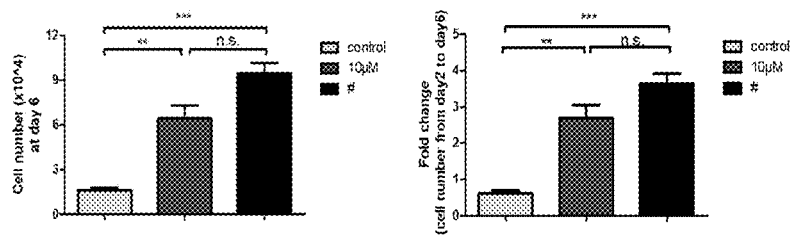
Figure 12F:
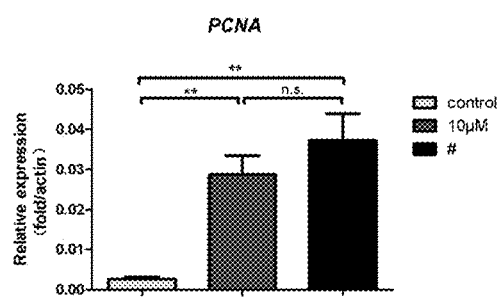
Figure 12G:
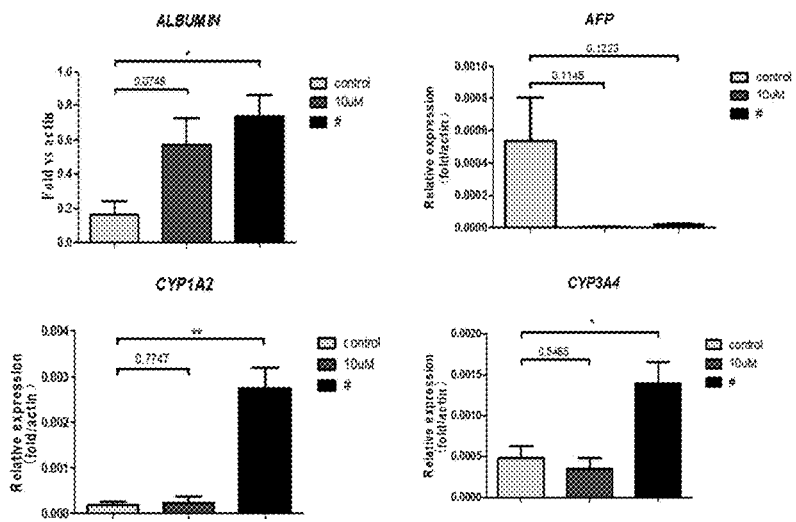
Figure 12H:
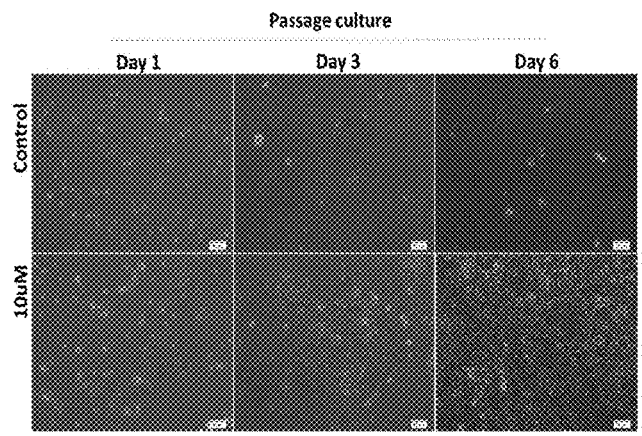
Figure 12I:
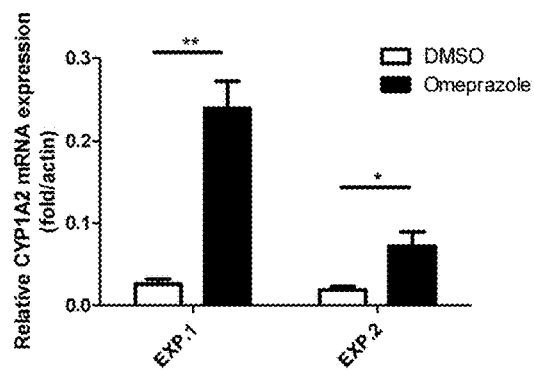

Results: three and a half years after liquid nitrogen cryopreservation of human embryonic hepatocytes, the recovery efficiency is about 5.8%. As shown in FIGS. 12(A) and 12(B), after 12 days of passage culture in small molecule medium (a total of 3 generations), the cells may be amplified by about 22.1 times (SD=4.2) in 10 μm small-molecule medium, and the cells may be amplified by about 13 times (SD=3.39) in 20 μM Bleb medium, as shown in FIG. 12 (B). At this time, the cell morphology is still typical hepatocyte morphology, showing an irregular polygon. However, after subculturing in the control medium, since most of the cells died after the first passage culture, the remaining small part of cells are cultured, and the amplification multiple is 58.3 times on day 12 (SD=13.9), but this time the cells are in the form of typical fibroblasts, with a slender and flat shape, as shown in FIG. 12(A). As shown in FIG. 12(C), real-time quantitative PCR is used to detect albumin (ALB, ALBUMIN) and alpha-fetoprotein (AFP, Alpha fetoprotein) of human hepatocyte-specific genes, the results show that human hepatocytes still express human hepatocyte-specific genes after 12 days of passage culture in 10 μM and 20 μM small molecule media; however, after 12 days of passage culture in control medium, very low albumin expression and no alpha-fetoprotein gene expression are detected in the obtained cells, indicating that the cells are not hepatocytes at this time, and this result is consistent with the results of FIGS. 12(A) and 12(B).

Example 8-2: Small Molecular Amplification of Adult Hepatocytes

Resuscitation and Culture of Adult Hepatocytes: adult hepatocytes (M00995-P Male human, Bioreclamation IVT) are taken out from the liquid nitrogen tank, quickly placing in a 37° C. water bath, after melting the cells are added to 5 ml of 37° C. pre-warmed hepatocyte inoculation medium (In VitroGRO CP Medium), then inoculating at $9\times10^4$/well in 24-well plate after counting, 2-4 hours after hepatocyte adherence, the hepatocyte inoculation medium is sucked and discarded, then respectively adding control medium for hepatocyte culture, 10 μm small molecule medium, and 20 μm small molecule medium; changing the medium every 2 days. The number of cells is estimated from the photograph on day 2. After 4 days, the 20 μm small molecule medium group is changed to culture the cells in 10 μm small molecule medium. After co-culturing for 6 days the cells are counted. A portion of the cells are taken for RNA extraction so as to detect the expression of human hepatocyte-specific genes.

Passage of Adult Hepatocytes: $4.7\times10^4$ hepatocytes cultured in in the above control group, and $8\times10^4$ hepatocytes cultured in 10 μm small molecule medium are respectively re-inoculated into 24-well plate coated with rat tail collagen, changing the medium every two days and culturing for 6 days, photographs are taken to record the growth of the cells.

Induction of CYP1A2 in Adult Hepatocytes Amplified by Small Molecule Medium: $3\times10^5$ hepatocytes are inoculated in 24-well plate coated with rat tail collagen, after culturing in 10 μm small molecule medium for 24 hours, the medium is replaced with 10 μm small molecule medium containing 50 μm omeprazole, and in the control group the cells are cultured in 10 μm small molecule medium containing DMSO; 48 hours later, the cells are collected to detect the expression of the CYP1A2 gene.

Results: the adherent efficiency of adult hepatocytes is similar at 5 hours after inoculation. After 2 days, in the control group, in 10 μm small molecule group and 20 μm small molecule group cells died in large number. Photographs are taken to estimate the number of living adherent cells ($2.53\times10^4$, SD=0.09). On day 4, amplification clones of the cells in the small molecule group begin to appear, while there is no significant amplification in the control group. Meanwhile, the medium in the 20 μm medium group is replaced with 10 μm small molecule medium (named as protocol #, i.e., culturing at 20 μm for 4 days, and culturing at 10 μm for 2 days). After two days of continuous culture, cell clones in the small molecule group are further amplified, while there is no significant change in the control group (FIG. 12(D)). After 6 days of culture, the number of cells is respectively $1.59\times10^4$ (SD=0.28) for the control group, $6.47\times10^4$ (SD=1.24) for the 10 μm group, and $9.47\times10^4$ (SD=0.98) for the # group. The multiple of cell amplification is obtained through dividing the cell number on day 6 by the cell number on day 2, and the results show that the small molecules have significant amplification effect on adult hepatocytes (FIG. 12(D) and FIG. 12(E)). The expression of proliferating cell nuclear antigen (PCNA) gene in the small molecule group is significantly higher than that in the control group, further demonstrating that small molecules have an effect on cell proliferation (FIG. 12(F)). Adult hepatocytes amplified with small molecules still express human hepatocyte specific genes ALBUMIN, AFP, CYP1A2, CYP3A4 (FIG. 12(G)). The 10 um small molecule medium can subculture human hepatocytes, while the control medium cannot subculture human hepatocytes (FIG. 12(H)). Subcultured adult hepatocytes may increase the expression of CYP1A2 gene after induction with omeprazole, suggesting that hepatocytes amplified with small molecules are still functional (FIG. 12(I)).

Example 9-1: Bleb Inhibits TGF-Beta-Mediated Activation of Myofibroblasts and Expression of Fibrosis-Related Proteins Excessive activation of myofibroblasts during fibrosis is the primary cellular mechanism leading to the symptoms of fibrosis. During the injury process, pro-fibrogenic factors (such as cytokines and inflammatory factors, etc.) promote the transformation of fibroblasts, pericytes, adult stem or progenitor cells, endothelial cells and epithelial cells in the vicinity of the injured site into myofibroblasts. This myofibroblast excessively proliferates, contracts and synthesizes and secretes a large amount of extracellular matrix, mainly including collagen. This causes the tissue to harden to form fibrosis, hindering the regeneration and repair of the tissue or organ, and seriously impairing the function of the tissue or organ. Among them, transforming growth factor beta 1 (TGF-β1) is one of the most important and effective growth factors leading to activation and fibrosis of myofibroblasts.

Figure 13A:
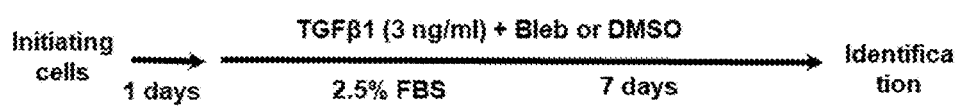
Figure 13B:
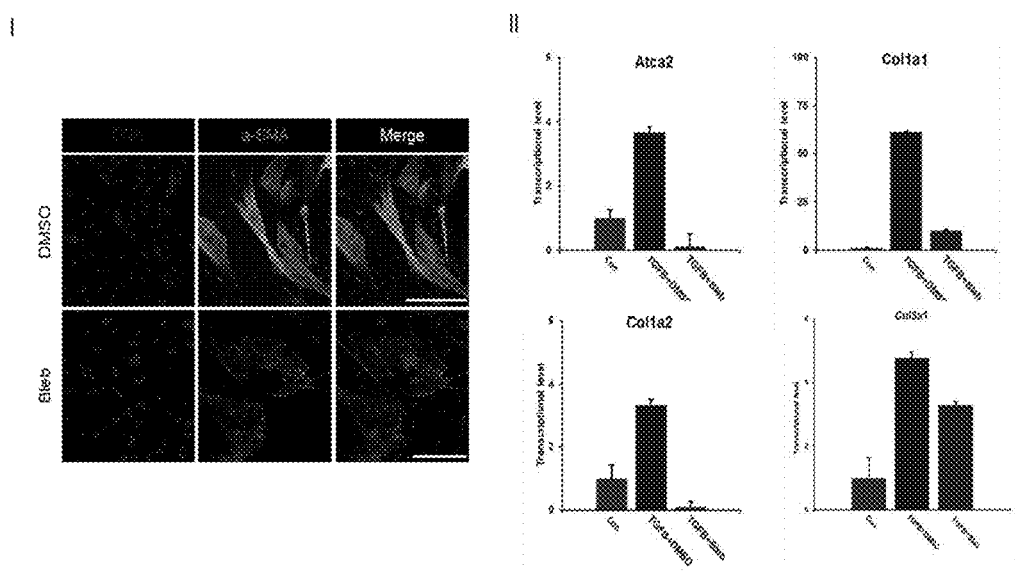
Figure 13C:
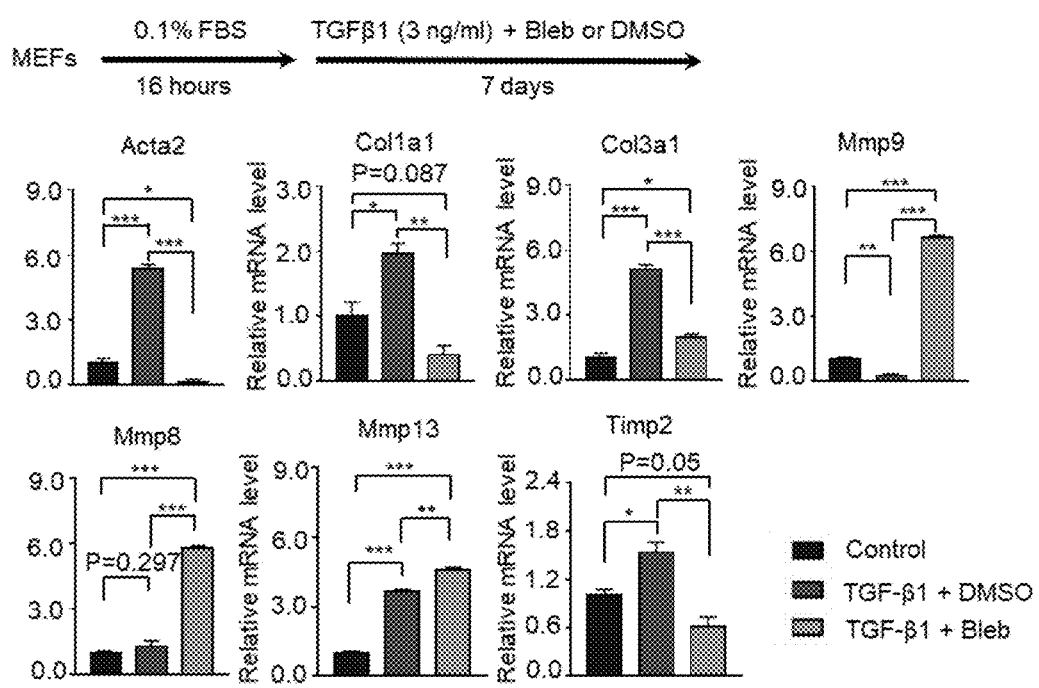
Figure 13D:
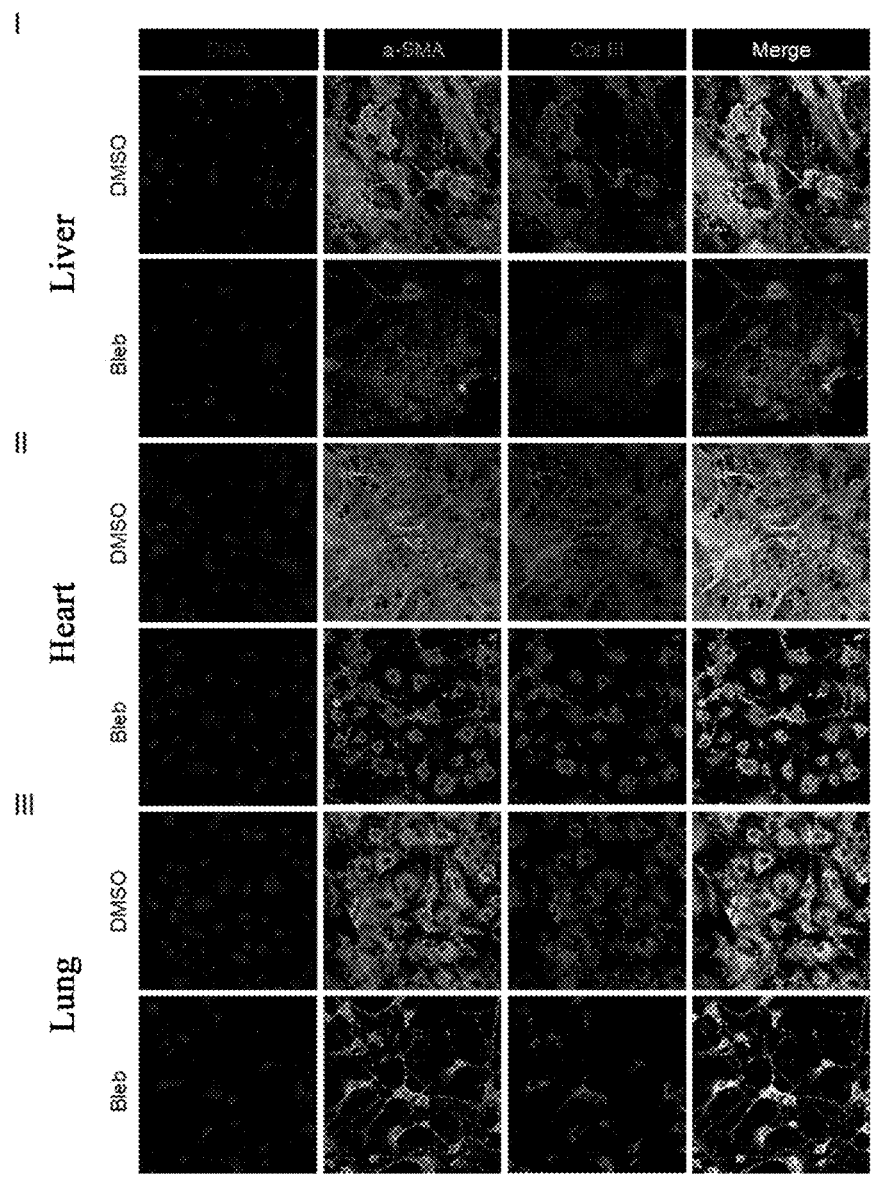
Figure 13E:
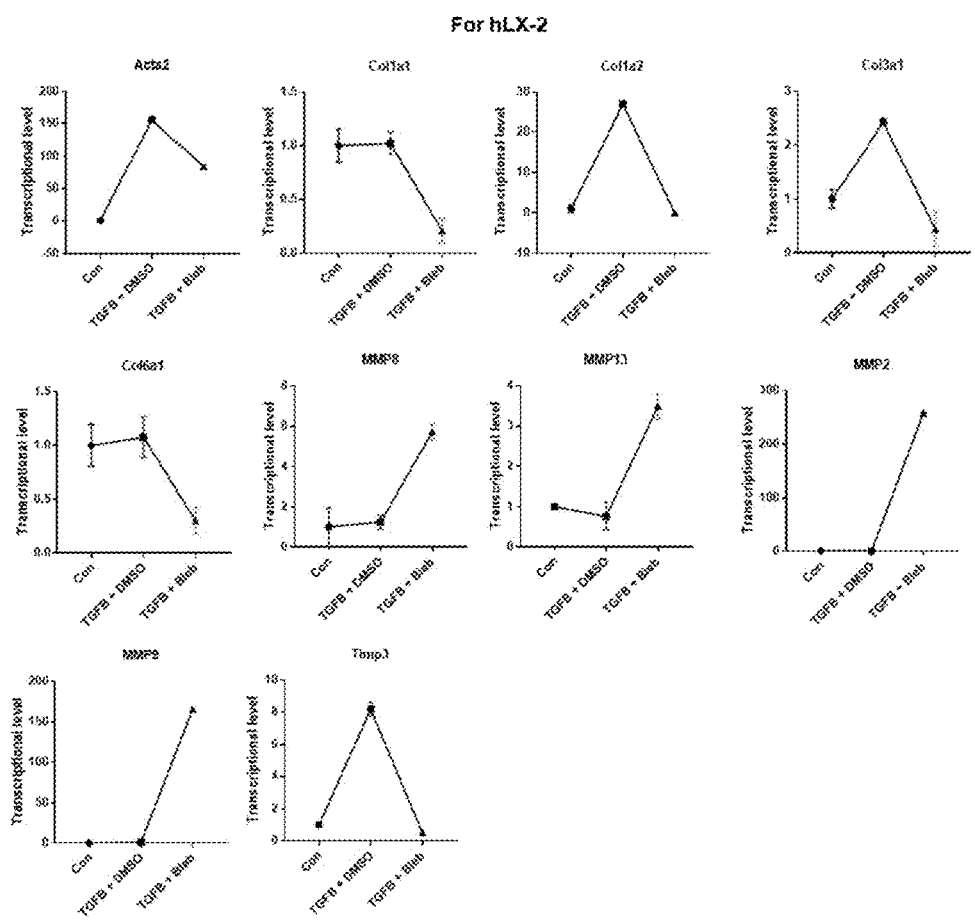
Figure 13F:
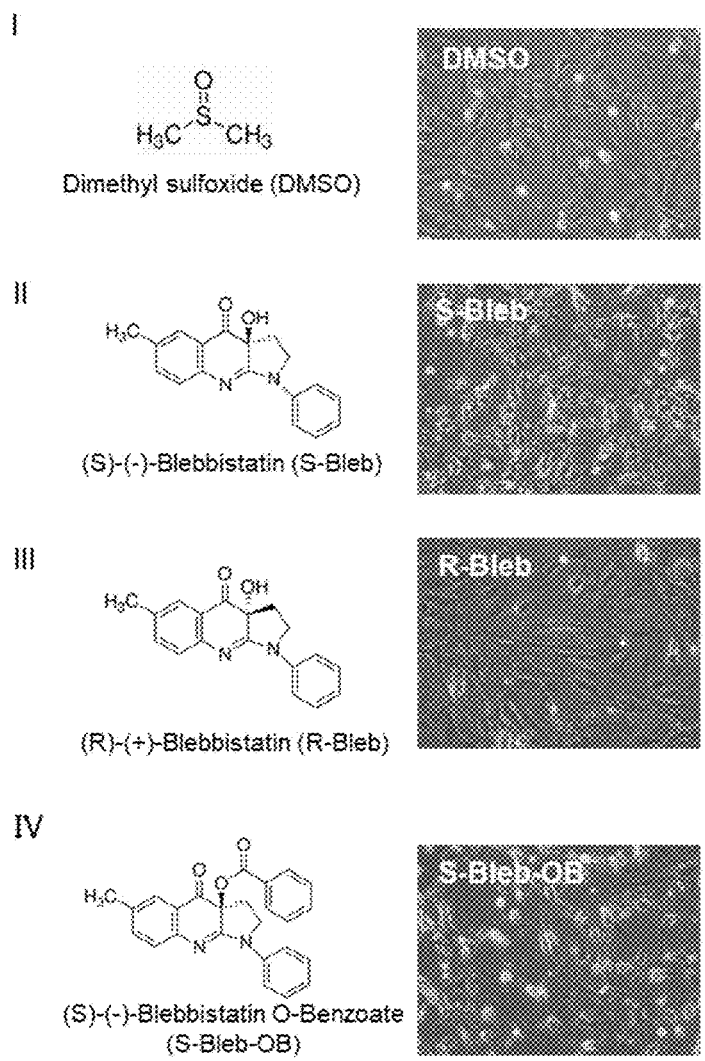

In this example, cell models for in vitro fibrosis are respectively built to activate mouse hepatic stellate Cells (mHSCs, FIG. 13(B)), mouse embryonic fibroblasts (MEFs FIG. 13(C)), mouse adult liver, lung, and heart-derived primary mesenchymal cells (priMCs, FIG. 13(D)), and human hepatic stellate cells (hLX-2, FIG. 13(E)) into myofibroblasts through the induction of TGF-β1. The specific experimental procedure is as shown in FIG. 9A: a medium containing 10% serum is used for the initial cell culture; after 24 hours the medium is replaced with low serum medium (or pre-starvation treatment for 16 hours) while adding 3 ng/ml TGF-β1 with DMSO or Bleb (20 μM); after 7 days the expression of myofibroblast activation marker protein (Acta2), collagen (Col1a1, Col1a2, Col3a1, and Col1a2), and matrix metalloproteinases and inhibitors (collagenases: MmP8, and MmP13; gelatinases: MmP2, and MmP9; a metalloproteinase inhibitor: Timp1/2/3) are identified.

The above experimental results show that Bleb significantly inhibits TGF-β1 induced transformation of the mouse astrocytes (mHSCs) into myofibroblasts and extracellular matrix synthesis, as shown in FIG. 13(B). Furthermore, FIG. 13(C) shows that Bleb significantly inhibits TGF-β1 induced transformation of mouse MEFs into myofibroblasts and extracellular matrix synthesis. The results in FIG. 13(D) show that, Bleb significantly inhibits TGF-β1 induced transformation of primary mesenchymal cells derived from different mouse organs into myofibroblasts and extracellular matrix synthesis. The results in FIG. 13(E) show that, Bleb significantly inhibits TGF-β1 induced transformation of the human astrocytes (hLX-2) into myofibroblasts and extracellular matrix synthesis, while promoting the up-regulation of metalloproteinases for degrading extracellular matrix and down-regulation of its inhibitors.

In summary, Bleb significantly inhibits transformation of various mouse or human mesenchymal cells (including hepatic stellate cells, fibroblasts, visceral mesenchymal cells, etc.) into myofibroblasts and extracellular matrix synthesis, while promoting the up-regulation of metalloproteinases for degrading extracellular matrix and down-regulation of its inhibitors, thereby inhibiting fibrosis during injury. This effect is conservative across different species and different mesenchymal cell types.

Figure 13G:
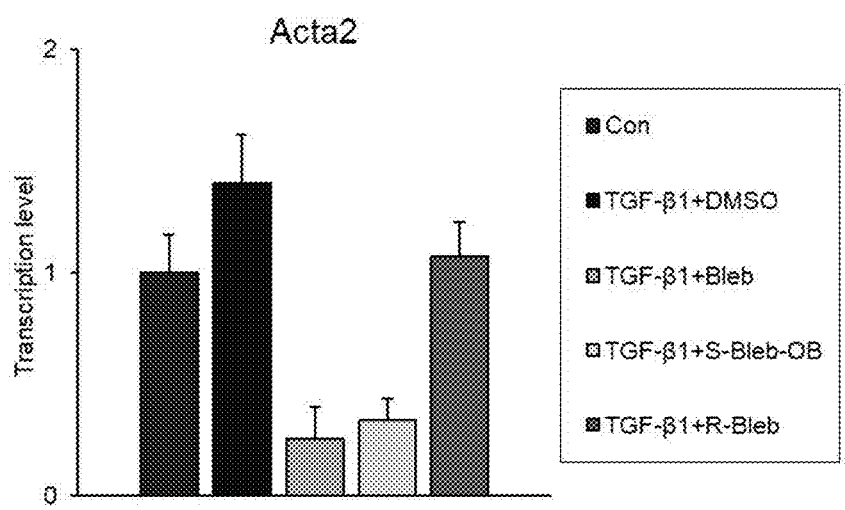

Example 9-2: Bleb Derivatives and Fibrous Actin (F-Actin) Assembly Inhibitors can Inhibit TGF-Beta-Mediated Myofibroblast Activation and Expression of Fibrosis-Related Proteins The effect of Bleb ((S)-(−)-blebbistatin) derivatives is further evaluated, and the evaluation scheme is as described in Example 9-1, and it is found that as compared with DMSO, Bleb may destroy the stretched state of MEFs (I and II in FIG. 13(F)). The inactive enantiomer (R)-(+)-blebbistatin (abbreviated as R-Bleb) does not affect the fibrous morphology of MEFs, and has no inhibitory effect on TGF-β1-induced myofibroblast activation, as shown in FIG. 13(G), indicating that the chiral hydroxyl group is necessary for Bleb to inhibit fibrotic activity (III in FIG. 13(F)). The experimental results show that another derivative (S)-(−)-blebbistatin o-benzoate (S-Bleb-OB) (20 µM) also has good activity and may destroy the stretched state of MEFs cells (IV in FIG. 13(F)), and it is also capable of inhibiting TGF-β1-induced myofibroblast activation, as shown in FIG. 13 (G). This suggests that new derivatives produced by modification of Bleb may have better biological activity than Bleb.

Bleb targets myosin, which is one of the main components of actomyosin, and actomyosin is the main structural basis for the contractile force of cells. This shows that myosin constitutes the actomyosin cytoskeleton system, and may be used as an effective target for inhibiting myofibroblast activation and fibrosis of tissue or organ.

The foregoing merely illustrates the principle of the invention. It should be understood that the scope of the present invention is not intended to be limited to the exemplary aspects described herein, but should include all currently known and future developed equivalents. In addition, it should be noted that a number of improvements and modifications may be made without departing from the spirit of the invention, and such improvements and modifications should also be considered within the scope of the invention.

The invention claimed is:

1. A method for reducing pulmonary fibrosis or muscle fibrosis, which comprises: administering (−)-blebbistatin or (−)-blebbistatin o-benzoate to a subject in need thereof.

2. The method according to claim 1, wherein:
the pulmonary fibrosis is a pulmonary fibrosis caused by inhalation of inorganic dust, radiation damage, inhalation of organic dust, drug damage or other causes; and idiopathic pulmonary fibrosis; and
the muscle fibrosis is a muscle fibrosis caused by a genetic factor or a congenital factor.

* * * * *